United States Patent [19]

Ostermayer et al.

[11] Patent Number: 4,460,580
[45] Date of Patent: Jul. 17, 1984

[54] N-ALKYLATED AMINOALCOHOLS AND THEIR PHARMACEUTICAL COMPOSITIONS USEFUL FOR THE TREATMENT OF CARDIAC INSUFFICIENCY

[75] Inventors: Franz Ostermayer; Markus Zimmermann, both of Riehen, Switzerland

[73] Assignee: Ciba-Geigy Corporation, Ardsley, N.Y.

[21] Appl. No.: 391,814

[22] Filed: Jun. 24, 1982

Related U.S. Application Data

[63] Continuation-in-part of Ser. No. 316,263, Oct. 29, 1981, abandoned, which is a continuation-in-part of Ser. No. 095,688, Nov. 19, 1979, abandoned, which is a continuation-in-part of Ser. No. 041,570, May 23, 1979, abandoned.

[30] Foreign Application Priority Data

Jun. 5, 1978 [CH] Switzerland ............... 6136/78

[51] Int. Cl.$^3$ ............... C07D 213/56; A61K 31/44
[52] U.S. Cl. ............... 424/232; 424/230; 544/238; 544/335; 544/336; 546/291; 546/337; 548/128; 548/136; 548/195; 548/236; 548/342; 549/77; 549/494; 564/165
[58] Field of Search ............... 546/337, 291; 424/230, 424/232; 564/165

[56] References Cited

U.S. PATENT DOCUMENTS

| | | | |
|---|---|---|---|
| 3,816,516 | 6/1974 | Cox et al. | 260/559 S |
| 4,012,444 | 3/1977 | Lunts et al. | 260/559 S |
| 4,146,638 | 3/1979 | Renth et al. | 424/304 |

Primary Examiner—Henry R. Jiles
Assistant Examiner—Bernard Dentz
Attorney, Agent, or Firm—Irving N. Feit; Michael W. Glynn

[57] ABSTRACT

The invention relates to novel N-alkylated aminoalcohols of the formula

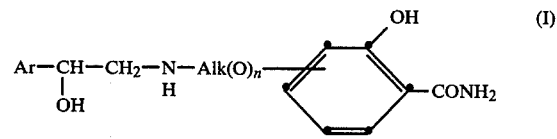

in which Ar is a radical of aromatic character which is unsubstituted or substituted by hydroxyl, n has the values nought or 1 and Alk is an alkylene radical having 2 to 5 carbon atoms and the nitrogen atom and the oxygen atom or, if n is nought, the salicylamide radical are separated from one another by at least two carbon atoms in the straight-chain, and their salts. The main action of the novel compounds consists in a stimulation of cardiac β-receptors; the compounds also effect a blockage of adrenergic α-receptors and a lowering in the blood pressure. They can therefore be used as β-stimulators, especially as agents having a positively inotropic action for the treatment of cardiac insufficiency. Compounds of the formula I in which Ar is phenyl, unsubstituted or substituted by 1 or 2 hydroxyl groups, Alk is an alkylene radical having 2 to 4 carbon atoms, n has the value 1, and the nitrogen atom and the oxygen atom are separated from one another by at least 2 carbon atoms in the straight-chain, or salts thereof, exhibit effects on the central nervous system, which are reflected for example in the suppression of the symptoms of impaired sympathetic functions and in the suppression of lack of initiative. Such compounds of the formula I therefore can be used for the treatment of reactive or endogenic states of depression of varying degrees of severity, and also for the treatment of neurotic or other psychic disturbances involving loss of initiative and depressive disorders. Such compounds can also be used for the short-term treatment of postpartum or postoperative depression, or of depression of different origin. Such compounds of the formula I can be used on their own or in combination with other antidepressants.

41 Claims, No Drawings

N-ALKYLATED AMINOALCOHOLS AND THEIR PHARMACEUTICAL COMPOSITIONS USEFUL FOR THE TREATMENT OF CARDIAC INSUFFICIENCY

This is a continuation-in-part of our copending application Ser. No. 316,263, filed Oct. 29, 1981, abandoned, which in turn is a continuation-in-part of our application No. 095,688 filed Nov. 19, 1979, abandoned, which in turn is a continuation-in-part of our application Ser. No. 041,570, filed May 23, 1979, abandoned.

The present invention relates to novel N-alkylated aminoalcohols of the formula

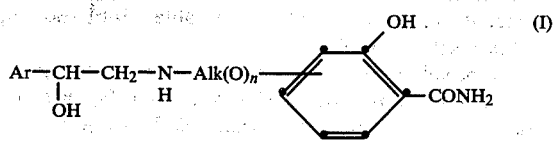

in which Ar is a radical of aromatic character which is unsubstituted or substituted by hydroxyl, n has the values nought or 1 and Alk is an alkylene radical having 2 to 5 carbon atoms and the nitrogen atom and the oxygen atom or, if n is nought, the salicylamide radical are separated from one another by at least two carbon atoms in the straight-chain, and their salts, processes for their preparation and pharmaceutical preparations contaning such compounds and the use thereof.

A radical of aromatic character Ar is, in particular, a monocyclic carbocyclic or heterocyclic radical of aromatic character having 5 to 6 ring members and at most 3 hetero-atoms, in particular nitrogen, oxygen and/or sulfur atoms, as ring members. A radical Ar is, therefore, in particular phenyl or also pyridyl, pyridazinyl, pyrimidinyl, pyrazinyl, furyl, pyrryl, thienyl, oxazolyl, thiazolyl, pyrazolyl, imidazolyl or thiadiazolyl.

The group of the formula

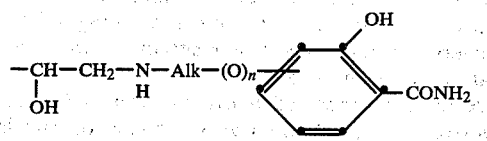

is bonded to a carbon atom in a radical Ar and can assume any one of the possible positions. In a phenyl radical substituted by a hydroxyl group, the said group is preferably in the 4-position. The radical of the formula

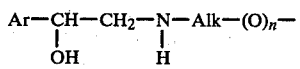

can substitute the salicylamide ring in any one of the possible positions.

Alkylene Alk can be straight-chain or branched and is, for example, 1,2-ethylene, 1,2-, 2,3- or 1,3-propylene, 1,4- or 2,4-butylene or 2-methyl-2,4-butylene, the carbon atom bonded to the nitrogen atom preferably being branched.

Pyridyl is 2-, 3- or 4-pyridyl; pyridazinyl is 3- or 4-pyridazinyl; pyrimidinyl is 2-, 4- or 5-pyrimidinyl whilst pyrazinyl is 2-pyrazinyl. Furyl is 2- or 3-furyl; pyrryl is 2- or 3-pyrryl; thienyl is 2- or 3-thienyl, whilst oxazolyl is 2- or 4-oxazolyl, thiazolyl is 2-, 4- or 5-thiazolyl, pyrazolyl is 3- or 4-pyrazolyl, imidazolyl is 2- or 4-imidazolyl and thiadiazolyl is 1,2,4-thiadiazol-3- or -5-yl or 1,3,4-thiadiazol-2-yl.

Salts of the compounds of the formula I are in particular acid addition salts and especially pharmaceutically acceptable, non-toxic acid addition salts with suitable inorganic acids, such as hydrochloric acid, hydrobromic acid, sulfuric acid or phosphoric acid, or with suitable organic aliphatic, cycloaliphatic, aromatic, araliphatic or heterocyclic carboxylic or sulfonic acids, such as formic acid, acetic acid, propionic acid, succinic acid, glycollic acid, lactic acid, malic acid, tartaric acid, citric acid, ascorbic acid, maleic acid, fumaric acid, pyruvic acid, benzoic acid, anthranilic acid, 4-hydroxybenzoic acid, salicylic acid, phenylacetic acid, embonic acid, methanesulfonic acid, ethanesulfonic acid, hydroxyethanesulfonic acid, ethylenesulfonic acid, 4-chlorobenzenesulfonic acid, toluenesulfonic acid, naphthalenesulfonic acid, sulfanilic acid or cyclohexylaminesulfonic acid.

Because of the close relationship between the novel compounds in the free form and in the form of their salts, what is stated in this specification in respect of the free compounds and in respect of the salts also applies by analogy to the corresponding salts and free compounds.

The novel compounds possess valuable pharmacological properties. The main action of the novel compounds consits in a stimulation of cardiac β-receptors, and this can be demonstrated, for example, in the heart as a positively inotropic and positively chronotropic action. Thus, in concentrations of from about 0.3 ng/ml an increase in frequency and concentration power is effected in an isolated guineapig atrium.

The positively inotropic and chronotropic action can also be demonstrated in vivo (narcotised cats) as an increase in the maximum rate of pressure rise in the left ventricle (dp/dt) and in the heart rate when from about 0.3 μg/kg are administered intravenously. Individual compounds display a clearly preferential inotropic action. The novel compounds also effect a blockage of adrenergic α-receptors, which, for example, can be shown with amounts of from about 100 ng/ml as an inhibition of the noradrenaline contraction in an isolated seminal duct of a rat. Moreover, a lowering in the blood pressure is effected by the novel compounds and this can be shown with amounts of from about 0.003 mg/kg after intravenous administration to narcotised cats. Some of the novel compounds of the formula I, in particular those, in which n has the value 1 show distinctly preferential stimulation of the β₁-receptors of the heart over the β₂-receptors in blood vessels and the trachea and are accordingly to be regarded as cardio-selective β-stimulators.

The novel compounds can thus be used as β-stimulators, especially as agents having a positively inotropic action for the treatment of cardiac insufficiency, on their own or in combination with other preparations, for example cardiac glycosides.

Compounds of the formula I in which Ar is phenyl, unsubstituted or substituted by 1 or 2 hydroxyl groups, Alk is an alkylene radical having 2 to 4 carbon atoms, n has the value 1, and the nitrogen atom and the oxygen atom are separated from one another by at least 2 carbon atoms in the straight-chain, exhibit effects on the central nervous system, which are reflected for example in the suppression of the symptoms of impaired sympathetic functions and in the suppression of lack of initiative, as can be demonstrated for example by virtue of the antagonism against hypothermia induced in mice after s.c.-administration of 2 mg/kg of reserpine (B. Benz et al,: Arzneimittelforschung 21, 654–61 (1971)) in a dose range of about 0,0003 mg/kg to about 30 mg/kg i.p., or by virtue of the antagonism against hypothermia induced in mice after s.c.-administration of 10 mg/kg of apomorphine (Puech A. L.: Europ.J. of Pharmacol. 47, 125–127(1978); Schelkunov E. L.: Psychopharmacol. 55, 87–95, (1977)) in a dose range of about 0,025 mg/kg to about 10 mg/kg i.p., or by virtue of the antagonism against hypothermia induced in mice after i.p.-administration of 0,25 mg/kg of clonidine (Voigtleander P. F. et al,: Neuropharmacol. 17, 375–81 (1978)) in a dose range of about 0,01 mg/kg to about 1 mg/kg i.p. With respect to these results such compounds of the formula I can be used for the treatment of reactive or endogenic states of depression of varying degrees of severity, and also for the treatment of neurotic or other psychic disturbances involving loss of initiative and depressive disorders. Such compounds can also be used for the short-term treatment of post-partum or postoperative depression, or of depression of different origin. Such compounds of the formula I can be used on their own or in combination with other antidepressants.

The invention relates in particular to compounds of the formula I in which Ar is phenyl or pyridyl, for example 2- or 3- or 4-pyridyl, or pyridazinyl, for example 3- or 4- or 6-pyridazinyl, or pyrimidinyl, for example 2- or 4- or 5-pyrimidinyl, or pyrazinyl, for example 2-pyrazinyl, or furyl, for example 2- or 3-furyl, or pyrryl, for example 2- or 3-pyrryl, or thienyl, for example 2- or 3-thienyl, or oxazolyl, for example 2- or 4-oxazolyl, or thiazolyl, for example 2- or 4-thiazolyl, or pyrazolyl, for example 3- or 5-pyrazolyl, or imidazolyl, for example 2- or 4-imidazolyl, or thiadiazolyl, such as 1,2,4-thiadiazol-3- or -5-yl or 1,3,4-thiadiazol-2-yl, which radicals are in each case unsubstituted or substituted by 1 or 2 hydroxyl groups, and Alk is an alkylene radical having 2 to 4 carbon atoms and the nitrogen atom and the oxygen atom or, if n is nought, the salicylamide radical are separated from one another by 2 to 3 carbon atoms in the straight-chain, and n is nought or 1, or salts thereof, especially pharmaceutically acceptable, non-toxic acid addition salts thereof.

The invention relates in particular to compounds of the formula I in which Ar is phenyl, 2- or 3-pyridyl, 2- or 3-furyl or 2- or 3-thienyl, which radicals are in each case unsubstituted or substituted by 1 or 2 hydroxyl groups, and Alk is an alkylene radical with 2 to 4 carbon atoms and the nitrogen atom and the oxygen atom or, if n is nought, the salicylamide radical are separated from one another by 2 to 3 carbon atoms in the straight-chain, and n is nought or 1, or salts thereof, especially pharmaceutically acceptable non-toxic acid addition salts thereof.

The invention also relates in particular to the following compounds of the formula I in which Ar is phenyl, 2- or 3-pyridyl, which radicals are in each case unsubstituted or substituted by 1 or 2 hydroxyl groups, and Alk is an alkylene radical having 2 to 4 carbon atoms, and the nitrogen atom and the oxygen atom, or, if n is nought, the salicylamide radical are separated from one another by at least 2 carbon atoms in the straight-chain, and n is nought or 1, or salts thereof, especially pharmaceutically acceptable, non-toxic acid addition salts thereof.

The invention relates in particular to compounds of the formula I in which Ar is phenyl, unsubstituted or substituted by 1 or 2 hydroxyl groups, Alk is an alkylene radical having 2 to 4 carbon atoms, n has the value 1, and the nitrogen atom and the oxygen atom are separated from one another by at least 2 carbon atoms in the straight-chain, or salts thereof, especially pharmaceutically acceptable, non-toxic acid addition salts thereof.

The invention relates specifically to the compounds of the formula I named in the example, or salts thereof, especially pharmaceutically acceptable, non-toxic acid addition salts thereof.

The invention relates in particular to compounds of the formula I, in which Ar and Alk have the meaning defined above and n has the value 1, or salts thereof, especially pharmaceutically acceptable, non-toxic acid addition salts thereof.

The novel compounds of the formula I are prepared in a manner known per se. They can be obtained, for example, by reacting a compound of the formula

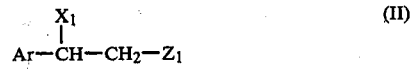

with a compound of the formula

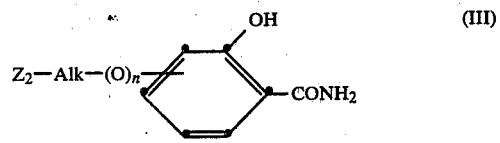

in which formulae one of the groups $Z_1$ and $Z_2$ is a reactive esterified hydroxyl group and the other is a primary amino group and $X_1$ is hydroxyl, or $X_1$ and $Z_1$ together are in epoxy group and $Z_2$ is a primary amino group, and Ar, Alk and n are as defined above, and/or, if desired, converting a resulting free compound into a salt or converting a resulting salt into a free compound and/or, if desired, separating a resulting mixture of isomers into the isomers or resolving a resulting racemate into the antipodes.

A reactive esterified hydroxyl group $Z_1$ or $Z_2$ is a hydroxyl group esterified by a strong acid, especially a strong inorganic acid, such as a hydrogen halide acid, especially hydrochloric acid, hydrobromic acid or hydriodic acid, or sulfuric acid, or a strong organic acid, especially a strong organic sulfonic acid, such as an aliphatic or aromatic sulfonic acid, for example methanesulfonic acid, 4-methylphenylsulfonic acid or 4-bromophenylsulfonic acid, and is, in particular, halogen, for example chlorine, bromine, or iodine, or aliphatically or aromatically substituted sulfonyloxy, for example methylsulfonyloxy or 4-methylphenylsulfonyloxy.

The above reaction is carried out in a manner per se and, especially when a starting material containing a reactive esterified hydroxyl group is used, is advantageously carried out in the presence of a basic agent, such as an inorganic base, for example an alkali metal carbonate or hydroxide or alkaline earth metal carbonate or hydroxide, or an organic basic agent, such as an alkali metal lower alkanolate, and/or an excess of the basic reactant, and customarily in the presence of a solvent or solvent mixture and, if necessary, with cooling or warming, for example in a temperature range of from about −20° C. to about +150° C., in an open or closed vessel and/or in an inert gas atmosphere, for example in a nitrogen atmosphere.

Starting materials of the formula II or III are known or can be prepared in a manner known per se. Thus, a compound of the formula Ar—H in which any hydroxyl groups which may be present can be protected by a protective group, for example one of those described below, can be halogenacetylated on a carbon atom of the radical Ar using a halogenacetyl halide, for example chloroacetyl chloride, in the presence of a suitable Lewis acid, for example aluminium chloride, by the Friedel-Crafts method and the carbonyl group in the Ar-halogenoacetyl compound thus obtainable can be reduced to the carbinol group, for example by treatment with a suitable hydride reducing agent; if desired, a halogen $Z_1$ can be converted to a primary amino group $Z_1$, for example by treatment with ammonia or a suitable derivative thereof, such as hexamethylenetetramine, and decomposition of the resulting compound with a dilute mineral acid, or by reaction with an alkali metal salt of phthalimide and splitting of the resulting N-phthalimide compound, for example with hydrazine. Starting materials of the formula II in which $X_1$ and $Z_1$ together are epoxy can be obtained, for example, by cyclising a compound of the formula II in which $X_1$ is hydroxyl and $Z_1$ is a reactive esterified hydroxyl group, such as chlorine or methanesulfonyloxy, by means of alkaline reagents, for example a mixture of dilute sodium hydroxide solution and tetrabutylammonium chloride in a suitable solvent, for example methylene chloride. Starting materials of the formula III can be obtained, for example, by reacting a hydroxysalicylamide with a dihalogenoalkane which corresponds to the definition of Alk, such as a chloro-bromo- or dibromo-alkane, in the presence of an alkaline condensing agent, such as an alkali metal carbonate. These reactions are carried out in the conventional manner and protective groups present on the hydroxyl groups are detached at the same time or as described below.

The compounds of the formula I can also be prepared when, in a compound of the formula

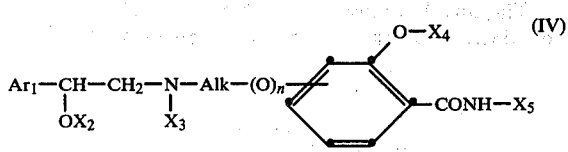

in which $Ar_1$ has the meaning defined for Ar or is a radical Ar which is substituted by 1 to 2 groups which can be converted to hydroxyl and $X_2$, $X_3$ and $X_4$ are each hydrogen or a substituent replaceable by hydrogen and $X_5$ is hydrogen, or $X_2$ and $X_3$ and/or $X_4$ and $X_5$ together are a divalent radical replaceable by two hydrogen atoms, with the proviso that at least one of the radicals $X_2$, $X_3$ and $X_4$ differs from hydrogen, or at least $Ar_1$ is a radical Ar which is substituted by 1 to 2 groups which can be converted to hydroxyl, or at least $X_2$ and $X_3$ together or $X_4$ and $X_5$ together are a divalent radical replaceable by two hydrogen atoms, or in a salt thereof, the $X_2$, $X_3$ or $X_4$ and $X_5$ together which differ from hydrogen are replaced by hydrogen and/or substituted hydroxyl present in a radical $Ar_1$ is converted to free hydroxyl and, if desired, the additional process steps are carried out.

The detaching of the groups $X_2$, $X_3$ or $X_4$ or, in each case, $X_2$ and $X_3$ or $X_4$ and $X_5$ together and of the hydroxyl substituents present in a radical $Ar_1$ is effected by means of solvolysis, such as hydrolysis, alcoholysis or acidolysis, or by means of reduction, including hydrogenolysis.

A particularly suitable detachable group $X_3$ and $X_4$ and also hydroxyl protective groups in a radical $Ar_1$ is, in particular, a hydrogenolytically detachable α-aryl-lower alkyl group, such as a substituted or unsubstituted 1-polyphenyl-lower alkyl or 1-phenyl-lower alkyl group, in which substituents, especially in the phenyl moiety, can be, for example, lower alkyl, such as methyl, or lower alkoxy, such as methoxy, and in particular benzyl. A group $X_3$ and especially $X_2$ and $X_4$ and also hydroxyl protective groups in a radical $Ar_1$ can also be a solvolytically, such as hydrolytically or acidolytically, detachable radical and also a radical detachable by reduction, including hydrogenolysis, especially a corresponding acyl radical, such as the acyl radical of an organic carboxylic acid, for example lower alkanoyl, such as acetyl, or aroyl, such as benzoyl, and also the acyl radical of a half-ester of carbonic acid, such as lower alkoxycarbonyl, for example methoxycarbonyl, ethoxycarbonyl or tert.-butoxycarbonyl, 2-halogeno-lower alkoxycarbonyl, for example 2,2,2-trichloroethoxycarbonyl or 2-iodoethoxycarbonyl, substituted or unsubstituted 1-phenyl-lower alkoxycarbonyl, for example benzyloxycarbonyl or diphenylmethoxycarbonyl, or aroylmethoxycarbonyl, for example phenacyloxycarbonyl, and also a substituted or unsubstituted 1-polyphenyl-lower alkyl group, in which substituents, in particular in the phenyl moiety, are, for example, as defined above, and in particular trityl.

A detachable radical formed by $X_2$ and $X_3$ and/or $X_4$ and $X_5$ together is, in particular, a hydrogenolytically detachable group, such as substituted or unsubstituted 1-phenyl-lower alylidene, in which substituents, especially in the phenyl moiety, can be, for example, lower alkyl or lower alkoxy, and especially benzylidene, and also solvolytically, especially hydrolytically, detachable groups, such as lower alkylidene, for example methylene or isoproplidene, or 1-phenyl-lower alkylidene in which the phenyl moiety is unsubstituted or substituted by lower alkyl, such as methyl, or lower alkoxy, such as methoxy, especially benzylidene or cycloalkylidene, for example cyclopentylidene or cyclohexylidene.

Starting materials which can be used in the form of salts are, in particular, used in the form of acid addition salts, for example with mineral acids and also with organic acids.

Hydrogenolytically detachable radicals $X_2$, $X_3$ and/or $X_4$, especially substituted or unsubstituted 1-phenyl-lower alkyl groups, and also suitable acyl groups, such as substituted or unsubstituted 1-phenyl-lower alkoxycarbonyl, and also substituted or unsubstituted 1-phenyl-lower alkylidene groups formed by the groups $X_2$ and $X_3$ or also $X_4$ and $X_5$ together, as well as hydroxyl protective groups of this type which are present in a radical $Ar_1$, can be detached by treatment with catalytically activated hydrogen, for example with hydrogen in the presence of a nickel catalyst, such as Raney nickel, or of a suitable noble metal catalyst.

Hydrolytically detachable groups $X_2$, $X_3$ and/or $X_4$, such as acyl radicals of organic carboxylic acids, for example lower alkanoyl, and half-esters of carbonic acid, for example lower alkoxycarbonyl, and also, for example, trityl radicals, as well as lower alkylidene, 1-phenyl-lower alkylidene or cycloalkylidene groups formed by the radicals $X_2$ and $X_3$ and/or $X_4$ and $X_5$ together, as well as hydroxyl protective groups of this type which are present in a radical $Ar_1$, can, depending on the nature of such radicals, be detached by treatment with water under acid or basic conditions, for example in the presence of a mineral acid, such as hydrochloric acid or sulfuric acid, or of an alkali metal hydroxide or carbonate or alkaline earth metal hydroxide or carbonate or of an amine, such as isopropylamine.

Acidolytically detachable radicals $X_2$, $X_3$ and/or $X_4$ and/or hydroxyl protective groups in a radical $Ar_1$ are, in particular, certain acyl radicals of half-esters of carbonic acid, for example tert.-lower alkoxycarbonyl or substituted or unsubstituted diphenylmethoxycarbonyl radicals, and also tert.-lower alkyl radicals; these can be detached by treatment with suitable strong organic carboxylic acids, such as lower alkanecarboxylic acids which are unsubstituted or substituted by halogen, especially fluorine, in particular with trifluoroacetic acid (if necessary in the presence of an activating agent, such as anisole) and also with formic acid.

Radicals $X_2$, $X_3$ and/or $X_4$ and/or hydroxyl protective groups in a radical $Ar_1$ which can be detached by reduction are also to be understood as meaning those groups which are detached on treatment with a chemical reducing agent (especially with a reducing metal or a reducing metal compound). Such radicals are, in particular, 2-halogeno-lower alkoxycarbonyl or arylmethoxycarbonyl, which can be detached, for example, by treatment with a reducing heavy metal, such as zinc, or with a reducing heavy metal salt, such as chromium-II salt, for example chromium-II chloride or chromium-II acetate, usually in the presence of an organic carboxylic acid, such as formic acid or acetic acid, and of water.

Protective groups which are located on any hydroxyl groups which may be present in a radical $Ar_1$ correspond to the groups which have been mentioned above and are detachable by means of the methods described and replaceable by hydrogen, such groups being detached, in the course of the process described, at the same time as other groups, or subsequently in a separate process measure.

The above reactions are usually carried out in the presence of a solvent or solvent mixture, it being possible for suitable reactants at the same time also to act as solvents, and, if necessary, with cooling or warming, for example in an open or closed vessel and/or in the atmosphere of an inert gas, for example nitrogen.

The starting materials of the formula IV can be obtained in a manner known per se, by reacting a compound of the formula $Ar_1$—H with a halogenacetyl halide, for example chloroacetyl chloride, in the presence of a suitable Lewis acid, for example aluminium chloride, by the Friedel-Crafts method, reducing the carbonyl group in the $Ar_1$-halogenoacetyl compound which is obtained in this way, or in another conventional manner, to the carbinol group, for example by means of sodium borohydride, and reacting the resulting compound with an amine of the formula

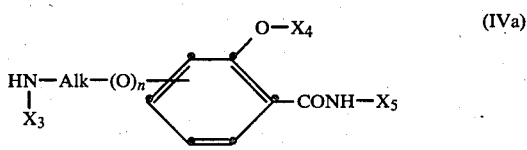
(IVa)

in which $X_3$ is as defined and $X_4$, or $X_4$ and $X_5$ together, differ from hydrogen.

It is also possible, for example, to reduce the Schiff's base formed by reacting a compound of the formula

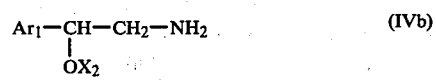
(IVb)

with a carbonyl compound of the formula

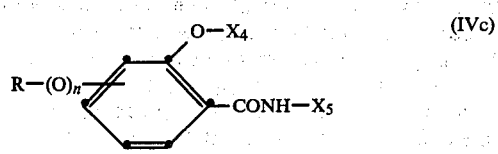
(IVc)

in which R is an alkyl radical which corresponds to the alkylene radical Alk and contains a carbonyl grouping which is separated from the oxygen atom or the phenyl radical by at least one carbon atom and $X_4$, or $X_4$ and $X_5$ together, are one of the indicated protective groups, with a borohydride, such as sodium borohydride, to give a compound of the formula IV. The reduction can also be effected by means of activated hydrogen in the presence of a hydrogenation catalyst, for example of a platinum-on-charcoal catalyst.

Carbonyl compounds of the formula (IVc), in turn, can be obtained in a conventional manner by reacting a compound of the formula

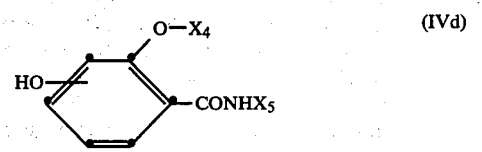
(IVd)

with a compound of the formula R—Hal (IVe), in which R is as defined above, and a compound (IVe), for example a halogenoketone, for example chloroacetone.

The novel compounds of the formula I can also be obtained when, in a compound of the formula

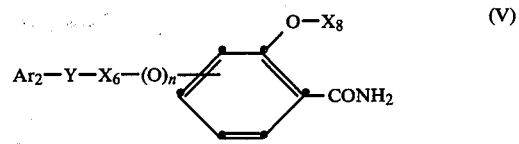
(V)

in which $X_6$ is a reducible group of the formulae —CH=N—Alk— (Va) or —CH$_2$—N=Alk$_1$ (Vb) or —C(=X$_7$)—N(X$_8$)—Alk— (Vc) or —CH$_2$—N(X$_8$)—C(=X$_7$)—Alk$_2$— (Vd) or a group —CH$_2$—N(X$_8$)—Alk— (Ve), in which formulae Alk$_1$ is an alkyl-ylidene radical corresponding to a radical Alk and Alk$_2$ corresponds to a radical Alk shortened by a methylene group bonded to the nitrogen atom, $X_7$ is an oxo or thioxo radical and $X_8$ is hydrogen or a radical replaceable by hydrogen under the conditions for the reduction of $X_6$ and/or Y, and Y is a radical of the formula —CO— (Vf) or —CH(OX$_8$)— (Vg), in which $X_8$ is as defined above, Ar$_2$ corresponds to a radical Ar but can carry one or two groups OX$_8$, in which $X_8$ is as defined above, in place of one or two hydroxyls, and n is nought or 1 and, in every case, $X_6$ is a reducible group Va to Vd and/or Y is a carbonyl group Vf, this group or groups is or are reduced and, in the same operation, the groups $X_8$ which differ from hydrogen are replaced by hydrogen and, if desired, the additional process steps are carried out.

A hydrogenolytically detachable group $X_8$ is, in particular, an α-aryl-lower alkyl group, such as a substituted or unsubstituted 1-phenyl-lower alkyl group, in which substituents can be, for example, lower alkoxy, such as methoxy, and is very particularly benzyl.

Protective groups which are located on hydroxyl groups which may be present as substituents on the radical $Ar_2$ correspond to the groups which have been mentioned above for $X_8$ and are detachable by means of the methods described and replaceable by hydrogen, such groups being detached, in the course of the process described, at the same time as other groups, or subsequently in a separate process measure.

Starting materials of the formula V containing a group $X_6$ of the formula Vb can also be in the isomeric form of ring tautomers of the formula

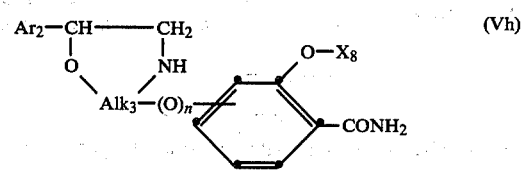

in which $Alk_3$ has the meaning defined for $Alk_1$ and the oxygen atom and nitrogen atom are bonded to the same carbon atom.

An alkyl-ylidene group $Alk_1$ is, for example, methine or ethyl-ylidene, whilst an alkylidene group $Alk_2$ is, for example, methylene, ethylidene or 1-methyl-ethylidene.

The reduction of the nitrogen-carbon double bond in starting materials of the formula V which contain a group Va or Vb as $X_6$, whilst $Ar_2$, Y, $X_8$ and n are as defined under formula V (or of the oxygen-carbon-nitrogen bond in the isomeric compounds of the formula Vg) to a nitrogen-carbon single bond can be effected in a manner known per se, for example by treatment with catalytically activated hydrogen, such as hydrogen in the presence of a suitable hydrogenation catalyst, for example of a nickel, platinum or palladium catalyst, hydrogenolytically detachable groups $X_8$ being detached and replaced by hydrogen at the same time; alternatively the reduction is carried out with a suitable hydride reducing agent, such as an alkali metal borohydride, for example sodium borohydride. In all cases a carbonyl radical Y, if such is present, is also reduced to a hydroxymethylene radical at the same time as the group Va or Vb is reduced and, if hydride reducing agents are used, acyl radicals of carboxylic acids, for example acetic acid, bonded to oxygen can also be present as radicals $X_8$ and detached in the same operation.

The reduction of the carbonyl group Y in starting materials of the general formula V which contain a group Ve as the radical $X_6$, whilst $Ar_2$, $X_8$ and n are as defined under formula V, can be effected in the manner indicated above for the reduction of groups Va and Vb, it again being possible for corresponding radicals $X_8$ to be detached hydrogenolytically during the catalytic hydrogenation.

Hydride reducing agents, for example sodium borohydride, or diborane are particularly suitable for the reduction of compounds of the formula V which contain a group of the formula Ve or Vd and in which $Ar_2$, Y and n are as defined under formula V. The reduction of a carbonyl group Y, if this is present, and the detaching of acyl radicals of carboxylic acids, for example acetic acid, bonded, as radicals $X_8$, to oxygen are effected at the same time as the reduction of a group Vc or Vd. On the other hand, by restricting the amount of reducing agent and by suitable choice of the reduction conditions, care must be taken that the aromatically bonded carboxamide group is not reduced. Groupings of the formulae Ve and Vd in which $X_7$ in each case is a thioxo group are converted to the grouping of the formula —$CH_2$—NH—Alk— by reductive desulfurising, for example by treatment with a hydrogenation catalyst, such as Raney nickel. The above reduction reactions are carried out in a manner known per se, usually in the presence of an inert solvent and, if necessary, with cooling or warming, for example in a temperature range of from about $-20°$ to about $+150°$, and/or in a closed vessel under pressure and/or in an inert gas atmosphere, for example a nitrogen atmosphere.

A starting material of the formula V can be prepared in a manner known per se, if desired in situ, i.e. under the conditions of the process described. Thus, it is possible to acetylate a compound of the formula $Ar_2$—H (Vi) with an acetic acid halide or acetic acid anhydride in the presence of a Lewis acid and, in the resulting intermediate, then to convert the acetyl group to a glyoxyloyl group, for example by treatment with a suitable oxidising agent, such as selenium dioxide. A glyoxyl compound of this type or, if desired, a suitable derivative thereof, such as an acetal, can then be reacted with an amine of the formula

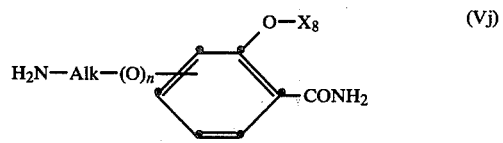

to give a starting material of the formula V in which the group $X_6$ has the formula Va, in which Y is a carbonyl group. It is also possible to halogenoacetylate a compound of the formula (Vi) with a halogenacetyl halide, for example chloroacetyl chloride, in the presence of a suitable Lewis acid, for example aluminium chloride, by the Friedel-Crafts method to give the corresponding $Ar_2$-chloroacetyl compound, to reduce the carbonyl group in the halogeno-acetyl compound obtainable in this way, or in another conventional manner, to a carbinol group by treatment with a suitable hydride reducing agent and to convert the halogen atom to a primary amino group by treatment with ammonia or a suitable derivative thereof, such as hexamethylenetetramine, and decomposition of the reaction product formed, using dilute acid, such as aqueous hydrochloric acid. By reacting the intermediate of the formula

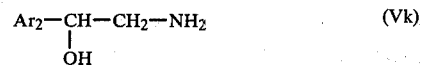

which is thus obtainable, with a carbonyl compound of the formula

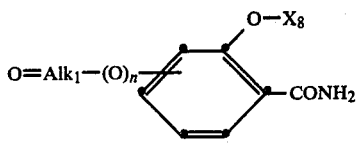 (VI)

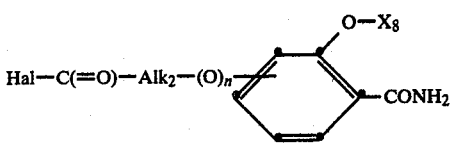 (Vo)

it is possible to obtain starting materials of the formula V in which the group $X_6$ has the formula (Vb). A modification of these reactions comprises replacing the halogen atom in the intermediate described above by reaction with a 1-aryl-lower alkylamine, for example benzylamine, or a di-(1-aryl-lower alkyl)-amine, for example dibenzylamine, by the corresponding 1-aryl-lower alkyl-amino or di-(1-aryl-lower alkyl)-amino group instead of replacing it, by treatment with ammonia and the like, by a primary amino group, and reacting the resulting compound, such as the corresponding dibenzylamino compound, with the oxo compound of the formula (VI) under the reducing conditions of the process. In this case, the reducing agent used is in particular catalytically activated hydrogen, for example hydrogen in the presence of a heavy metal hydrogenation catalyst or of a mixture thereof, such as of a palladium catalyst and/or platinum catalyst. Under such reaction conditions, hydrogenolytically detachable groups $X_8$, for example benzyl groups, are detached and the carbonyl group, if this is present, is reduced to the carbinol group and, at the same time, the nitrogen-carbon double bond is reduced to the corresponding nitrogen-carbon single bond.

In turn, oxo compounds of the formula (VI), in which n is 1, are obtainable, for example, by reacting a dihydroxy compound of the formula

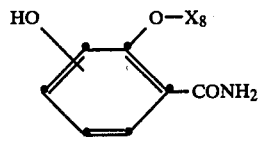 (Vm)

with a halogenoalkanone compound of the formula R—Hal (IVe) explained above, for example chloroacetone, in the presence of an alkaline condensing agent, such as potassium carbonate, or of an organic base, such as triethylamine.

Starting materials of the formula V in which the group $X_6$ has the formulae Vc or Vd can be prepared in a manner known per se, by, for example, reacting a formyl compound of the formula $Ar_2$—CHO (Vn) with hydrogen cyanide and, in the cyanohydrin intermediate thus obtainable, hydrolysing the cyano group to a carboxyl group, for example under acid conditions. The $Ar_2$-2-hydroxyacetic acid obtained in this way or via the intermediate stages of the imide-chloride, iminolower alkyl ester and lower alkyl ester is then reacted in the presence of a suitable condensing agent, for example of a carbodiimide, such as dicyclohexylcarbodiimide, with an amine of the formula (Vj), whereupon a starting material of the formula V in which the group $X_6$ has the formula (Vc) is obtained.

Furthermore, by reacting a compound of the formula Vk with a compound of the formula in which Hal is halogen and especially chlorine, a starting material of the formula (V) in which the group $X_6$ has the formula (Vd) can be obtained. It is also possible, in the $Ar_2$-chloracetyl compound indicated above, to replace the chlorine by a primary amino group, such as by reaction with hexamethylenetetramine, decomposing the product obtained by treatment with dilute mineral acid, and to react a compound thus obtained with a halogen compound of the formula (Vo). In a starting material of the formula V which is thus obtained and in which the group $X_6$ has the formula Vd and Y is a carbonyl group, the carbonyl group can be reduced to a carbinol group and, at the same time, the aliphatically bonded carbamoyl group can be reduced to a group of the formula

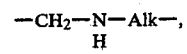

such as by means of a hydride reducing agent, especially diborane.

The novel compounds of the formula I can also be obtained by reacting a compound of the formula

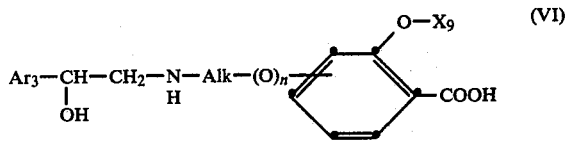 (VI)

in which $Ar_3$ has the meaning defined for Ar or is a radical Ar which is substituted by 1 to 2 groups convertible to hydroxyl by ammonolysis and $X_9$ is hydrogen or a group detachable by ammonolysis, or a reactive derivative of one of the carboxylic acids defined by formula VI, with ammonia and, at the same time, detaching any radicals $X_9$ which may be present and replacing these by hydrogen.

Hydrolytically and especially ammonolytically detachable radicals $X_9$ are acyl radicals or organic carboxylic acids, for example aroyl, such as benzoyl or lower alkanoyl, such as acetyl.

Reactive derivatives of the carboxylic acids defined by formula VI are, for example, the halides, such as the chlorides or bromides, and also the azides, as well as acid anhydrides, especially mixed acid anhydrides with, for example, lower alkanecarboxylic acids, such as acetic acid or propionic acid, or lower alkoxyalkanecarboxylic acids, such as 2-methoxyacetic acid. Reactive derivatives of the formula VI are, in particular, esters, for example with lower alkanols, such as methanol, ethanol, isopropanol or tert.-butanol, and also with aryl-lower alkanols, such as benzyl alcohol which is unsubstituted or substituted by lower alkyl, for example methyl, or lower alkoxy, for example methoxy, or phenols, which can be activated by suitable substituents, for example by halogen, such as 4-halogeno, such as 4-chloro, lower alkoxy, such as 4-lower alkoxy, such as 4-methoxy, 4-nitro or 2,4-dinitro, such as 4-chlorophenol, 4-methoxyphenol, 4-nitrophenol or 2,4-dinitrophenol, and also with cycloalkanols, such as cyclopentanol or cyclohexanol, which can be substituted by lower alkyl, for example methyl. The reaction is carried out in a manner known per se, usually in the presence of an inert solvent, for example in a temperature range of from about −10° to +50° C. in a closed vessel.

The starting materials of the formula VI can be obtained in a manner known per se, by brominating a compound of the formula $Ar_3—COCH_3$, reducing the carbonyl group in the $Ar_3$-halogenoacetyl compound thus obtained to a carbinol group, for example by means of diborane, and reacting the latter group with an amine of the formula

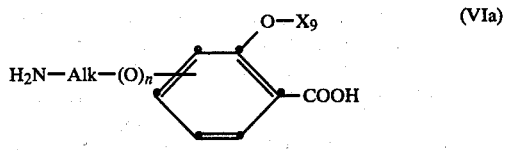

(VIa)

in which $X_9$ is as defined, or a reactive derivative thereof. It is also possible to react the $Ar_3$-halogenoacetyl compound with an amine of the formula VIa and subsequently to convert the carbonyl group to a carbinol group.

Furthermore, the Schiff's base formed by reacting a compound of the formula

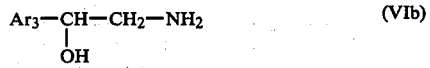

(VIb)

with a carbonyl compound of the formula

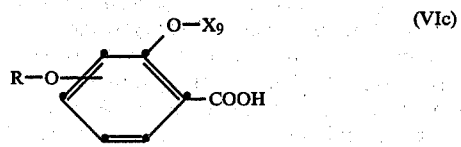

(VIc)

in which R is the alkyl radical which corresponds to an alkylene radical Alk and contains a carbonyl group, can be reduced with a borohydride, such as sodium borohydride. The reduction can also be effected by means of activated hydrogen in the presence of a hydrogenation catalyst, for example of a platinum-on-charcoal catalyst.

In turn, carbonyl compounds of the formula (VIc), in which n is 1, can be obtained by reacting a compound of the formula

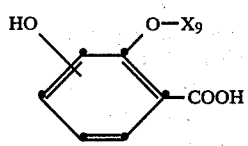

with a compound of the formula R—Hal (IVe), in which Hal is halogen, especially chlorine, in a manner known per se.

Depending on the process conditions and starting materials, the novel compounds are obtained in the free form or in the form of their salts, which also fall within the scope of the invention, and the novel compounds or salts thereof can also be in the form of hemi-, mono-, sesqui- or poly-hydrates thereof. Acid addition salts of the novel compounds can be converted to the free compounds in a manner known per se, for example by treatment with basic agents, such as alkali metal hydroxides, carbonates or bicarbonates or ion exchangers. On the other hand, resulting free bases can form acid addition salts with organic or inorganic acids, for example with the acids mentioned, the acids used to prepare these salts being, in particular, those which are suitable for forming pharmaceutically acceptable salts.

These or other salts, especially acid addition salts of the novel compounds, for example oxalates for perchlorates, can also be used to purify the resulting free bases, by converting the free bases to salts, separating these off and purifying them and liberating the bases again from the salts.

Depending on the choice of starting materials and procedures, the novel compounds can be in the form of optical antipodes or racemates or, if they contain at least two asymmetric carbon atoms, also in the form of mixtures of racemates. The starting materials can also be employed in the form of optical antipodes.

Resulting mixtures of racemates can be separated on the basis of the physico-chemical differences between the diastereoisomers into the two stereoisomeric (diastereomeric) racemates in a known manner, for example by chromatography and/or fractional crystallisation.

Resulting racemates can be resolved into the antipodes by methods known per se, for example by recrystallisation from an optically active solvent, by treatment with suitable micro-organisms or by reaction with an optically active substance which forms salts with the racemic compound, such substances being in particular acids, and separating the salt mixture obtained in this way, for example on the basis of different solubilities, into the diastereomeric salts, from which the free antipodes can be liberated by the action of suitable agents. Particularly commonly used optically active acids are, for example, the D- and L-forms of tartaric acid, di-o-toluenetartaric acid, malic acid, mandelic acid, camphorsulfonic acid, glutamic acid, aspartic acid or quinic acid. Advantageously, the more active of the two antipodes is isolated.

The invention also relates to those embodiments of the process in which a compound obtainable as an intermediate at any state of the process is used as the starting material and the missing process steps are carried out, or the process is discontinued at any stage, or in which a starting material is formed under the reaction conditions, or in which a reactant may be present in the form of its salts.

The starting materials used for carrying out the reactions according to the invention are preferably those which result in the groups of end products which have been mentioned in particular initially and especially which result in the end products specifically described or singled out.

The starting materials are known or, if they are novel, can be obtained by methods known per se, as described above, for example analogously to the procedures described in the examples. Novel starting materials are also a subject of the invention. The invention also relates to intermediates obtainable according to the process.

The novel compounds can be used, for example, in the form of pharmaceutical preparations which contain a pharmacologically effective amount of the active substance, if desired together with pharmaceutically usable carriers which are suitable for enteral, for example oral, or parenteral administration and can be inorganic or organic solid or liquid. Thus, tablets or gelatine capsules are used which contain the active ingredient together with diluents, for example lactose, dextrose, sucrose, mannitol, sorbitol, cellulose and/or glycerin and/or lubricants, for example silica, talc or stearic acid or salts thereof, such as magnesium stearate or calcium stearate, and/or polyethylene glycol. Tablets can also contain binders, for example magnesium aluminium silicate, starches, such as maize starch, corn starch, rice starch or arrowroot, gelatine, tragacanth, methylcellulose, sodium carboxymethylcellulose and/or polyvinylpyrrolidone, and, if desired, disintegrators, for example starches, agar or alginic acid or a salt thereof, such as sodium alginate, and/or effervescent mixtures, or adsorbents, dyes, flavourings and sweeteners. Furthermore, the novel pharmacologically active compounds can be used in the form of preparations which can be administered parenterally or in the form of infusion solutions. Such solutions are preferably isotonic aqueous solutions or suspensions and, for example in the case of lyophilised preparations which contain the active ingredient on its own or together with a carrier, for example mannitol, these can be prepared before use. The pharmaceutical preparations can be sterilised and/or contain adjuncts, for example preservatives, stabilisers, wetting agents and/or emulsifiers, solubilising agents, salts for regulating the osmotic pressure and/or buffers. The pharmaceutical preparations of this specification, which, if desired, can contain further pharmacologically active substances, are prepared in a manner known per se, for example by means of conventional mixing, granulating, sugar-coating, dissolving or lyophilising methods and contain from about 0,1% to 100% and especially from about 1% to about 50% of the active ingredient, lyophilisates containing up to 100% of the active ingredient.

The dosage can depend on various factors, such as the mode of administration, the species, the age and/or the individual condition. Thus, in the case of oral administration to warm-blooded animals weighing about 70 kg, the doses to be administered daily are preferably between about 0.005 and 0.1 g.

The following examples serve to illustrate the invention; temperatures are in degrees centigrade.

EXAMPLE 1

100 ml of isopropylamine are added to a solution of 40 g of crude α-[N-[2-(2,3-dihydro-2,2-dimethyl-4-oxo-4H-1,3-benzoxazin-6-yloxy)-1-methyl-ethyl]-aminomethyl]-benzyl alcohol in 450 ml of methanol and the mixture is refluxed for 1.5 hours. After evaporating the reaction mixture, a foam remains and this is dissolved hot in as little isopropanol as possible. After standing for several days, the crystals which have formed and which are a mixture of the diastereoisomers of α-[N-[2-(3-carbamoyl-4-hydroxy-phenoxy)-1-methyl-ethyl]-aminomethyl]-benzyl alcohol with a melting range of about 120°–150° are filtered off with suction. The pure enantiomer pairs which melt at 166°–168° and 152°–154° respectively are obtained by fractional recrystallisation from isopropanol.

The starting material is prepared as follows:
(a) 2,5-Dihydroxy-benzamide is converted by the method described by Irvine et al., Synthesis 1972, 568, using an excess of acetone, to 2,3-dihydro-2,2-dimethyl-6-hydroxy-4H-1,3-benzoxazin-4-one with a melting point of 215°–216°.
(b) 70 g of 2,3-dihydro-2,2-dimethyl-6-hydroxy-4H-1,3-benzoxazin-4-one in 400 ml of acetonitrile are stirred with 100 g of potassium carbonate and 32 ml of chloroacetone for 30 hours under reflux. After adding a further 3.2 ml of chloroacetone, the reaction mixture is heated for a further 15–20 hours. The reaction mixture is filtered whilst it is still warm, the residue is washed thoroughly with acetone and the combined filtrate is evaporated. The crystalline residue is recrystallised from toluene and yields 2,3-dihydro-2,2-dimethyl-6-(2-oxo-propoxy)-4H-1,3-benzoxazin-4-one with a melting point of 125°–126°.
(c) A solution of 26.6 g of 2,3-dihydro-2,2-dimethyl-6-(2-oxo-propoxy)-4H-1,3-benzoxazin-4-one and 14.6 g of α-(aminomethyl)-benzyl alcohol in 450 ml of methanol is hydrogenated under normal conditions, with the addition of 50 mg of concentrated sulfuric acid and 4 g of platinum-on-charcoal catalyst, until 1 mol equivalent of hydrogen has been taken up. The solution which is obtained after filtering off the catalyst and which contains the crude α-[N-[2-(2,3-dihydro-2,2-dimethyl-4-oxo-4H-1,3-benzoxazin-6-yloxy)-1-methyl-ethyl]-aminomethyl]-benzyl alcohol is hydrolysed without working up.
(d) The compound used in Example 1 can also be obtained analogously to Example 2(c) by reduction, using sodium borohydride, of the Schiff's base obtained from the ketone obtained according to Example 1b and α-(aminomethyl)-benzyl alcohol.

EXAMPLE 2

18 g of crude α-[N-[2-(2,3-dihydro-2,2-dimethyl-4-oxo-4H-1,3-benzoxazin-7-yloxy)-1-methyl-ethyl]-aminomethyl]-benzyl alcohol are dissolved in 100 ml of isopropanol, 50 ml of isopropylamine are added and the mixture is refluxed for 1.5 hours. After evaporating, the reaction mixture is partitioned between 50 ml of 2N hydrochloric acid and 100 ml of ether and the aqueous phase is separated off, rendered alkaline with concentrated ammonia solution and extracted with 3 times 150 ml of ethyl acetate.

After evaporating, a foam is obtained which crystallises on the addition of isopropanol. α-[N-[2-(4-Carbamoyl-3-hydroxy-phenoxy)-1-methyl-ethyl]-aminomethyl]-benzyl alcohol is obtained as a mixture of diastereomers with a melting range of 140°–156°. The two enantiomer pairs with a melting point of 171°–173° and 149°–151° respectively are obtained by fractional crystallisation from methanol.

The starting material is prepared as follows:
(a) 2,3-Dihydro-2,2-dimethyl-7-hydroxy-4H-1,3-benzoxazin-4-one with a melting point of 249°–251° is obtained analogously to Example 1(a) from 2,4-dihydroxybenzamide.
(b) Analogously to Example 1(b), 2,3-dihydro-2,2-dimethyl-7-(2-oxopropoxy)-4H-1,3-benzoxazin-4-one with a melting point of 160°–162° (from isopropanol) is obtained from 168 g of 2,3-dihydro-2,2-dimethyl-7-hydroxy-4H-1,3-benzoxazin-4-one, 305 g of potassium carbonate and 88 ml of chloroacetone in 1.2 liters of acetonitrile by boiling for 28 hours and then working up.
(c) A mixture of 13.0 g of 2,3-dihydro-2,2-dimethyl-7-(2-oxo-propoxy)-4H-1,3-benzoxazin-4-one and 6.9 g of α-(aminomethyl)-benzyl alcohol is refluxed with 100 ml of ethanol for 5 hours. 5.7 g of sodium borohydride are then added in portions, with ice-cooling and stirring, and the reaction mixture is then stirred at room temperature overnight. The excess sodium borohydride is then destroyed with 2N hydrochloric acid (about 75 ml), with ice-cooling, and the reaction mixture is concentrated. The aqueous phase is rendered alkaline with concentrated ammonia solution and the product which has precipitated is extracted with twice 500 ml of ethylacetate.

The crude α-[N-[2-(2,3-dihydro-2,2-dimethyl-4-oxo-4H-1,3-benzoxazin-7-yloxy)-1-methyl-ethyl]-aminomethyl]-benzyl alcohol obtained by evaporating is hydrolysed without further purification.

EXAMPLE 3

A mixture of 25.4 g of α-(aminomethyl)-benzyl alcohol and 11.1 g of 2,3-dihydro-2,2-dimethyl-6-(2-bromoethoxy)-4H-1,3-benzoxazin-4-one is melted and the melt is stirred in a bath at 130° for 3 hours. After cooling, the reaction mixture is dissolved in 50 ml of isopropanol and the solution is diluted with about 50 ml of ethyl acetate, whereupon α-[N-[2-(3-carbamoyl-4-hydroxy-phenoxy)-ethyl]-aminomethyl]-benzyl alcohol with a melting point of 172°–174° crystallised out. After recrystallisation from 300 ml of ethanol, the product melts at 174°–175°.

The starting material is prepared as follows:

(a) A mixture of 48.2 g of 2,3-dihydro-2,2-dimethyl-6-hydroxy-4H-1,3-benzoxazin-4-one, 70 g of potassium carbonate and 250 ml of 1,2-dibromoethane is refluxed for 4 hours with stirring. The slurry-like reaction mixture is extracted hot with 3–4 times 1 liter of methanol, the combined methanol extracts are evaporated and the residue is recrystallised from methanol. 55 g of 2,3-dihydro-2,2-dimethyl-6-(2-bromoethoxy)-4H-1,3-benzoxazin-4-one with a melting point of 190°–195° are obtained.

EXAMPLE 4

A solution of 15 g of crude N-[2-(4-carbamoyl-3-hydroxyphenoxy)-ethyl]-N-(2-hydroxy-2-phenylethyl)-benzylamine in 150 ml of methanol is hydrogenated under normal conditions, with the addition of 3 g of palladium-on-charcoal catalyst (5%), until the reaction has ceased. The catalyst is filtered off, the solvent is evaporated off and the residue is recrystallised from isopropanol. α-[N-[2-(4-Carbamoyl-3-hydroxy-phenoxy)-ethyl]-aminomethyl]-benzyl alcohol with a melting point of 141°–142° is obtained. The compound forms a hydrochloride with a melting point of 240°–242°.

The starting material is prepared as follows:

(a) 16.2 g of 2,3-dihydro-2,2-dimethyl-7-hydroxy-4H-1,3-benzoxazin-4-one are reacted analogously to Example 3(a) with 84 ml of 1,2-dibromoethane and yield 2,3-dihydro-2,2-dimethyl-7-(2-bromoethoxy)-4H-1,3-benzoxazin-4-one with a melting point of 156°–158° (from isopropanol).

(b) 53 g of 2,3-dihydro-2,2-dimethyl-7-(2-bromoethoxy)-4H-1,3-benzoxazin-4-one and 94 g of benzylamine are boiled for 3 hours, with stirring. The reaction mixture is rendered alkaline with concentrated ammonia and the organic phase is evaporated at a maximum of 50°.

The N-[2-(4-carbamoyl-3-hydroxy-phenoxy)-ethyl]-benzylamine thus obtained forms an oil, the hydrochloride of which melts at 252°–254° (from methanol).

(c) A mixture of 11.0 g of phenylethylene oxide, 9.2 g of N-[2-(4-carbamoyl-3-hydroxy-phenoxy)-ethyl]-benzylamine and 100 ml of isopropanol is refluxed for 10 hours. The reaction mixture is evaporated and the residue is stirred with 50 ml of hexane. The oil which is insoluble in hexane essentially consists of N-[2-(4-carbamoyl-3-hydroxyphenoxy)-ethyl]-N-(2-hydroxy-2-phenylethyl)-benzylamine, which is hydrogenated in the crude state.

EXAMPLE 5

A solution of 13.0 g of α-(aminomethyl)-3-pyridinemethanol and 26.5 g of 2,3-dihydro-2,2-dimethyl-6-(2-oxo-propoxy)-4H-1,3-benzoxazin-4-one in 400 ml of methanol is hydrogenated at 30° and under normal pressure with the addition of 0.1 ml of concentrated sulfuric acid and 1 g of platinum-on-charcoal catalyst (5%). Two further additions of, respectively, 1 g and 2 g of the same catalyst are required before the calculated amount of hydrogen has been taken up. After filtering off the catalyst, 50 ml of isopropylamine are added to the filtrate and the latter is refluxed for 1 hour and evaporated. The residue, which is a dark brown foam, is dissolved in 50 ml of methanol, 5.1 g of fumaric acid are added and the mixture is warmed until the fumaric acid has dissolved. After a prolonged time, α-[N-[2-(3-carbamoyl-4-hydroxy-phenoxy)-1-methyl-ethyl]-aminomethyl]-3-pyridinemethanol crystallises out in the form of the neutral fumarate with a melting point of 192°–196° (sinters above 187°), in which one enantiomer pair is greatly enriched (~80%).

EXAMPLE 6

Crude α-[N-[2-(3-carbamoyl-4-hydroxy-phenoxy)-1-methylethyl]-aminomethyl]-2-pyridinemethanol is obtained as a brown oil by a procedure which is analogous to that described in Example 5, but using 13.0 g of α-(aminomethyl)-2-pyridinemethanol. The product forms a neutral fumarate (from methanol) which melts at 147°–165° and is a mixture of the diastereomers.

EXAMPLE 7

A solution of 15.2 g of 4-benzyloxy-α-[N-[2-(3-carbamoyl-4-hydroxy-phenoxy)-1-methyl-ethyl]-aminomethyl]-benzyl alcohol in 500 ml of methanol is hydrogenated under normal conditions in the presence of 2 g of palladium-on-charcoal catalyst (5%) until 1 mol equivalent of hydrogen has been taken up. The catalyst is filtered off and the filrate is evaporated. The residual foam is partitioned between 300 ml of ethyl acetate and 50 ml of potassium bicarbonate solution and the organic phase is separated off, dried and evaporated. The crude α-[N-[2-(3-carbamoyl-4-hydroxy-phenoxy)-1-methyl-ethyl]aminomethyl]-4-hydroxybenzyl alcohol thus obtained forms a neutral fumarate with half the equivalent amount of fumaric acid in methanol and after a relatively long time this fumarate crystallises from acetone as a mixture of diastereomers with a melting point of 185°–195°. An enantiomer pair which are a single compound and have a melting point of 209°–212° (decomposition) can be obtained therefrom by fractional crystallisation from methanol.

The starting material is prepared as follows:

(a) A solution of 9.6 g of 2,3-dihydro-2,2-dimethyl-6-(2-oxo-propoxy)-4H-1,3-benzoxazin-4-one and 9.37 g of 4-benzyloxy-α-(aminomethyl)benzyl alcohol in 250 ml of methanol is hydrogenated analogously to Example 1 until one equivalent of hydrogen has been taken up. The catalyst is filtered off and, after adding 40 ml of isopropylamine, the solution is refluxed for 1 hour. Evaporation of the reaction mixture yields 4-benzyloxy-α-[N-[2-(3-carbamoyl-4-hydroxy-phenoxy)-1-methyl-ethyl]-aminomethyl-benzyl alcohol in the form of a crystalline mass which can be hydrogenated without further purification.

EXAMPLE 8

After adding 0.32 g of concentrated sulfuric acid and 3 g of platinum-on-charcoal catalyst (5%), a solution of 26.8 g of 5-(2-oxo-propoxy)-salicylamide and 17.6 g of α-(aminomethyl)-benzyl alcohol in 450 ml of methanol is hydrogenated under normal conditions until 1 mol equivalent of hydrogen has been taken up. The catalyst is filtered off, the solvent is evaporated and the crude α-[N-[2-(3-carbamoyl-4-hydroxy-phenoxy)-1-methyl-ethyl]aminomethyl]-benzyl alcohol thus obtained is dissolved hot in as little methanol as possible and the solution is cooled and seeded with crystals of the enantiomer pair having the higher melting point. The crystals with a melting point of 160°-163° which are obtained after standing for several days yield, after a further crystallisation from methanol, one pur enantiomer pair with a melting point of 166°-168°. The enantiomer pair which has the lower melting point of 152°-154° is isolated from the first mother liquor after evaporating off the solvent, by fractional crystallisation using ethyl acetate or isopropanol.

The 5-(2-oxo-propoxy)-salicylamide required as a starting material is prepared as follows:

(8a) 74 g of crude 2,3-dihydro-2,2-dimethyl-6-(2-oxopropoxy)-4H-1,3-benzoxazin-4-one obtained according to Example 1b) are heated in a mixture of 150 ml of dioxan and 450 ml of 2N hydrochloric acid for 45 minutes on a waterbath. The solvent is evaporated and the crystalline residue is triturated with water and then filtered off with suction. Recrystallisation from isopropanol yields 5-(2-oxopropoxy)salicylamide with a melting point of 152°-154°.

EXAMPLE 9

A solution of 8.0 g of R-(−)-α-(aminomethyl)-benzyl alcohol and 12.2 g of 5-(2-oxo-propoxy)-salicylamide in 220 ml of methanol is hydrogenated and worked up analogously to Example 8. Neutralisation of the crude base with 5N hydrochloric acid in methanol yields, after recrystallisation from methanol/ether, the hydrochloride of R-(−)-α-[N-[2-(3-carbamoyl-4-hydroxy-phenoxy)-1-methylethyl]-aminomethyl]-benzyl alcohol in the form of the pure enantiomer with a melting point of 180°-184° ($[\alpha]_D^{20}$ −31±1° (1% in methanol)).

A mixture of the diastereomers with a melting point of 165°-180° crystallises out of the mother liquor on concentrating.

EXAMPLE 10

A solution of 7.2 g of 4-benzyloxy-α-[N-[2-(3-carbamoyl-4-hydroxy-phenoxy)-ethyl]-aminomethyl]-benzyl alcohol in 200 ml of methanol is hydrogenated analogously to Example 7 in the presence of palladium-on-charcoal catalyst (5%). Evaporation of the filtered solution yields crude α-[N-[2-(3-carbamoyl-4-hydroxyphenoxy)-ethyl]aminomethyl]-4-hydroxybenzyl alcohol, which after recrystallisation from methanol/isopropanol melts at 194°-196°.

The starting material is prepared as follows:

(a) A mixture of 21 g of α-(aminomethyl)-4-benzyloxybenzyl alcohol and 12 g of 6-(2-bromoethoxy)-2,3-dihydro-2,2-dimethyl-4H-1,3-benzoxazin-4-one is stirred in an oil bath at 130° for 1 hour. The reaction mixture is partitioned between 500 ml of ethyl acetate and 50 ml of 2N aqueous ammonia solution, the organic phase is separated off and evaporated and the residue is recrystallised from isopropanol. 4-Benzyloxy-α-[N-[2-(3-carbamoyl-4-hydroxy-phenoxy)-ethyl]-aminomethyl]-benzyl alcohol with a melting point of 160°-162° is obtained.

EXAMPLE 11

A molten mixture of 5.0 g of 6-(2-bromoethoxy)-salicylamide and 13.0 g of α-(aminomethyl)-benzyl alcohol is stirred in a bath at 130° for 1 hour. The reaction mixture is dissolved, whilst still warm, in 250 ml of ethyl acetate and the solution is washed successively with 50 ml of saturated potassium bicarbonate solution, 100 ml of water and 100 ml of saturated aqueous sodium chloride solution, dried over magnesium sulfate and evaporated. The residue is dissolved hot in 30 ml of ethanol, from which α-[N-[2-(2-carbamoyl-3-hydroxy-phenoxy)-ethyl]-aminomethyl]-benzyl alcohol with a melting point of 122°-123° crystallises out on cooling. The compound forms a hydrochloride with a melting point of 190°-191° (from methanol/isopropanol).

The starting material is prepared as follows:

(a) A mixture of 23.0 g of 2,6-dihydroxybenzamide, 20.7 g of potassium carbonate and 28.2 g of 1,2-dibromoethane in 300 ml of acetonitrile is stirred under reflux for 2-3 hours. The reaction mixture is filtered whilst still warm, the filtrate is evaporated and the residue is recrystallised from a little methanol. 6-(2-Bromoethoxy)salicylamide with a melting point of 120°-121° is obtained.

EXAMPLE 12

16.6 g of crude N-[3-(4-carbamoyl-3-hydroxyphenoxy)propyl]-N-(2-hydroxy-2-phenyl-ethyl)-benzylamine are hydrogenated analogously to Example 4 and the reaction mixture is worked up. α-[N-[3-(4-Carbamoyl-3-hydroxy-phenoxy)-propyl]-aminomethyl]-benzyl alcohol with a melting point of 208°-210° is obtained by recrystallisation from isopropanol.

The starting material is prepared by the following stages:

(a) A mixture of 38.6 g of 2,3-dihydro-2,2-dimethyl-7-hydroxy-4H-1,3-benzoxazin-4-one, 55.2 g of potassium carbonate, 47.2 g of 1-bromo-3-chloro-propane and 600 ml of acetone is refluxed for 24 hours. Filtering, concentrating the filtrate to ⅓ of the original volume and cooling yields 7-(3-bromopropoxy)-2,3-dihydro-2,2-dimethyl-4H-1,3-benzoxazin-4-one with a melting point of 111°-113°.

(b) 13.6 g of this compound are heated together with 32 g of benzylamine at 100° for 1½ hours, with stirring. Working up to give the base, analogously to Example 4b, and distilling off the excess benzylamine under a high vacuum yields, after recrystallisation of the residue from toluene, N-[3-(4-carbamoyl-3-hydroxy-phenoxy)-propyl]benzylamine with a melting point of 131°-135°.

(c) A solution of 12.7 g of N-[3-(4-carbamoyl-3-hydroxy-phenoxy)propyl]-benzylamine and 7.6 g of phenylethylene oxide in 80 ml of isopropanol is refluxed for 16 hours. The reaction mixture is evaporated, the residue is partitioned between 100 ml of 6N hydrochloric acid and 100 ml of ether and the aqueous phase is separated off and rendered alkaline with 2N ammonia solution. The N-[3-(4-carbamoyl-3-hydroxy-phenoxy)-propyl]-N-(2-hydroxy-2-phenyl-ethyl]-benzylamine thus obtained is isolated by extraction with ethyl acetate an debenzylated in the form of the crude product.

EXAMPLE 13

20 ml of concentrated ammonia solution are added to a solution of 1.7 g of crude α-[N-[2-(3-carbomethoxy-4-hydroxy-phenoxy)-1-methyl-ethyl]-aminomethyl]-benzyl alcohol in 10 ml of dioxan and the mixture is left to stand at room temperature for 60–70 hours. The reaction mixture is evaporated, the residue is dissolved in 75 ml of ethyl acetate and the solution is washed with 10 ml of saturated, aqueous sodium chloride solution. Evaporation of the organic phase yields crude α-[N-[2-(3-carbamoyl-4-hydroxy-phenoxy)-1-methyl-ethyl]aminomethyl]-benzyl alcohol as a mixture of diastereoisomers in the form of an oil and the latter is crystallised from a little ethyl acetate and is identical to the product obtained, for example, in Example 1; melting point 120°–140°.

The starting material is obtained as follows:
(a) A solution of 3.4 g of methyl 2,5-dihydroxybenzoate, 4.0 g of triethylamine and 2.8 g of chloroacetone in 40 ml of acetonitrile is refluxed for 16 hours. After adding 1.4 g of chloroacetone and 1.3 g of trietylamine, the reaction mixture is boiled for a further 5 hours and then evaporated, the residue is dissolved in 50 ml of toluene and the solution is washed with 10 ml of water and then with 10 ml of saturated aqueous sodium chloride solution and chromatographed over 200 g of silica gel. The fractions first eluted wih toluene contain methyl-5-(2-oxo-propoxy)-salicylate, which is recrystallised from isopropanol and melts at 80°–82°.
(b) A solution of 0.8 g of α-(aminomethyl)-benzyl alcohol and 1.2 g of methyl 5-(2-oxo-propoxy)-salicylate in 40 ml of methanol is hydrogenated analogously to Example 8.

On filtering and evaporating the filtrate, crude α-[N-[2-(3-carbomethoxy-4-hydroxy-phenoxy)-1-methyl-ethyl]-aminomethyl]-benzyl alcohol is obtained in the form of a yellowish oil, which is further processed as the crude product.

EXAMPLE 14

A solution of 13.4 g of phenylglyoxal and 19.6 g of 5-(2-aminoethoxy)-salicylamide in 100 ml of methanol is refluxed for 1 hour and 7 g of sodium borohydride are then added in portions, with stirring and ice-cooling. The reaction mixture is stirred overnight at about 20°, decomposed with 2N hydrochloric acid, with ice-cooling, and filtered. The filtrate is concentrated, rendered alkaline with concentrated ammonia solution and extracted with ethyl acetate.

The crude product obtained on evaporation is crystallised from ethanol and α-[N-[2-(3-carbamoyl-4-hydroxy-phenoxy)-ethyl]-aminomethyl]-benzyl alcohol with a melting point of 174°–175° is then obtained.

(14a) The 5-(2-aminoethoxy)-salicylamide with a melting point of 140°, which is required as a starting material, is obtained analogously to Example 21 by catalytic debenzylation of 5-(2-benzylaminoethoxy)-salicylamide by means of 5% palladium-on-charcoal catalyst in methanol.

EXAMPLE 15

Analogously to Example 3, α-[N-[2-(3-carbamoyl-4-hydroxyphenoxy)-ethyl]-aminomethyl]-2-pyridinemethanol with a melting point of 169°–170° (from ethanol/methaol) is obtained by melting 5.0 g of α-(aminomethyl)-2-pyridinemethanol and 2.2 g of 2,3-dihydro-2,2-dimethyl-6-(2-bromoethoxy)-4H-1,3-benzoxazin-4-one.

EXAMPLE 16

A mixture of 0,96 g of phenyl-ethylene oxide and 2.1 g of 4-(2-amino-propoxy)-salicylamide in 25 ml of 2-propanol is refluxed for 15 hours. The reaction mixture is then evaporated, the residue is partitioned between 10 ml of water and 100 ml of ethyl acetate and the organic phase is washed three times with water. On drying over magnesium sulfate and evaporating the organic phase, crude α-[N-[2-(4-carbamoyl-3-hydroxy-phenoxy)-1-methyl-ethyl]-aminomethyl]-benzyl alcohol is obtained and this is recrystallised analogously to Example 2 and in this way gives the two enantiomer pairs with a melting point of 171°–173° and 149°–151° respectively.

The starting material is prepared as follows:
(a) After adding about 5 g of Raney nickel catalyst, a solution of 25 g of 2,3-dihydro-2,2-dimethyl-7-(2-oxo-propoxy)-4H-1,3-benzoxazin-4-one in 500 ml of methanol is introduced into an autoclave and ammonia gas is then injected until the pressure is 5 bars. The solution is then hydrogenated at 50° and a hydrogen pressure of 100 bars until the reaction has ceased. After filtering off the catalyst and evaporating the solution, crude 4-(2-amino-propoxy)-salicylamide is obtained, which after recrystallisation from methanol melts at 185°–187°.

EXAMPLE 17

A mixture of 7.0 g of α-(aminomethyl)-2-furanmethanol and 7.5 g of 2,3-dihydro-2,2-dimethyl-6-(2-bromoethoxy)-4H-1,3-benzoxazin-4-one is melted and the melt is stirred for 1 hour in a bath at about 110°. 50 ml of isopropanol and 2 ml of concentrated ammonia solution are added to the reaction mixture whilst this is still warm, the mixture is boiled for 5 minutes and filtered and the filtrate is allowed to cool. After working up, α-[N-[2-(3-carbamoyl-4-hydroxyphenoxy)-ethyl]-aminomethyl]-2-furanmethanol with a melting point of 169°–171° is obtained.

EXAMPLE 18

A mixture of 2.7 g of α-(aminomethyl)-2-thiophenmethanol and 3.6 g of 2,3-dihydro-2,2-dimethyl-6-(2-bromoethoxy)-4H-1,3-benzoxazin-4-one is stirred together with 2 ml of triethylamine for 1 hour in a bath at 100°–110°. The reaction mixture is partitioned between 100 ml of ethyl acetate and 10 ml of 2N aqueous potassium bicarbonate solution and the organic phase is separated off, dried over magnesium sulfate and evaporated, yielding crude α-[N-[2-(3-carbamoyl-4-hydroxyphenoxy)-ethyl]-amino-methyl]-2-thiophen-methanol in the form of a crystalline mass which after recrystallisation from a little isopropanol melts at 158°–161°; repeated recrystallisation raises the melting point to 171°–172°.

EXAMPLE 19

Analogously to Example 8, a solution of 14.1 g of S-(+)-α-(aminomethyl)-benzyl alcohol and 21.5 g of 5-(2-oxo-propoxy)salicylamide in 400 ml of methanol is hydrogenated over 2 g of platinum-on-charcoal catalyst (5%), with the addition of 0.26 g of concentrated sulfuric acid, and the reaction mixture is worked up. The evaporation residue which is obtained as a foam crystallises from ethyl acetate as a mixture of diastereomers which has a melting point of 146°–161°. Fractional crystallisation from isopropanol yields a pure enantiomer of S-(+)-α-[N-[2-(3-carbamoyl-4-hydroxy-phenoxy)-1-methylethyl]-aminomethyl]-benzyl alcohol with a melting point of 160°–162°. Neutralisation, with methanolic hydrochloride acid, of the basic mother liquor obtained from the fractional crystallisation, and fractional crystallisation of the hydrochloride from methanol yields the other enantiomer in the form of the hydrochloride with a melting point of 181°–183°. In the form of the hydrochloride, both enantiomers have the same specific rotation $[\alpha]_D^{20} = +33° \pm 1°$ (C=1, methanol), but differ in respect of their $^{13}$C-NMR spectra.

EXAMPLE 20

A solution of 8.7 g of 4-benzyloxy-α-[N-[2-(4-carbamoyl-3-hydroxy-phenoxy)-ethyl]-aminomethyl]-benzyl alcohol in 100 ml of dioxan is hydrogenated under normal conditions with the addition of 2 g of palladium-on-charcoal catalyst (5%) until 1 equivalent of hydrogen has been taken up. The product which has precipitated is brought into solution after adding 200 ml of methanol, by warming, the catalyst is filtered off and the filtrate is evaporated. Recrystallisation of the residue from isopropanol yields crystalline α-[N-[2-(4-carbamoyl-3-hydroxy-phenoxy)-ethyl]-aminomethyl]-4-hydroxybenzyl alcohol with a melting point of 181°–182°.

(20a) The starting material can be prepared analogously to Example (10a) using 7-(2-bromoethoxy)-2,3-dihydro-2,2-dimethyl-4H-1,3-benzoxazin-4-one. The 4-benzyloxy-α-[N-[2-(4-carbamoyl-3-hydroxy-phenoxy)ethyl]-aminomethyl]-benzyl alcohol thus obtained melts at 181°–183°.

EXAMPLE 21

Analogously to Example 4, a solution of 45 g of crude α-[N-benzyl-N-[2-(3-carbamoyl-4-hydroxy-phenoxy)-ethyl]-aminomethyl]benzyl alcohol in 500 ml of methanol is hydrogenated with the addition of 5 g of palladium-on-charcoal catalyst (5%) and the reaction mixture is worked up. α-[N-[2-(3-Carbamoyl-4-hydroxy-phenoxy)-ethyl]aminomethyl]-benzyl alcohol with a melting point of 174°–175° (from ethanol) is obtained. The methanesulfonate melts at 182°–183° (from methanol).

The starting material is prepared as follows:

(21a) A suspension of 60 g of 6-(2-bromoethoxy)-2,3-dihydro-2,2-dimethyl-4H-1,3-benzoxazin-4-one in 110 ml of benzylamine is warmed for 30 minutes, with stirring, in a bath at 80°. The pH of the reaction mixture is then adjusted to about 3 using concentrated hydrochloric acid, with ice-cooling, and the mixture is left to stand to allow crystallisation to take place. After 4 hours, the crystals are filtered off with suction, washed with 100 ml of water and 100 ml of ethyl acetate and dried. The crude 5-(2-benzylamino-ethoxy)-salicylamide hydrochloride thus obtained melts at 214°–216°. The base liberated therefrom melts at 107°–108° (from ethyl acetate/ether).

(21b) A solution of 13.2 g of phenylethylene oxide and 28.6 g of 5-(2-benzylamino)-ethoxy)-salicylamide in 100 ml of isopropanol is refluxed for 24 hours. Evaporating off the solvent yields crude α-[N-benzyl-N-[2-(3-carbamoyl-4-hydroxy-phenoxy)-ethyl]-aminomethyl]benzyl alcoho in the form of an oil, which can be employed for debenzylation without further purification.

EXAMPLE 22

A mixture of 13.7 g of α-(aminomethyl)-benzyl alcohol and 9.4 g of 6-(3-bromopropoxy)-2,3-dihydro-2,2-dimethyl-4H-1,3-benzoxazin-4-one is heated for 45 minutes, with stirring, in a bath at 120°. The reaction mixture is cooled, 250 ml of ethyl acetate are added and the solution is washed twice in succession with 50 ml of aqueous, saturated potassium bicarbonate solution, 50 ml of water and 50 ml of saturated sodium chloride solution, dried over magnesium sulfate and evaporated. The oily residue is dissolved in a little isopropanol and the solution is neutralised with a solution of hydrogen chloride gas in methanol (∼5N). α-[N-[3-(3-Carbamoyl-4-hydroxy-phenoxy)-propyl]-aminomethyl]-benzyl alcohol is thus obtained in the form of the hydrochloride with a melting point of 189°–192°.

The starting material is prepared as follows:

(22a) A mixture of 9.7 g of 2,3-dihydro-2,2-dimethyl-6-hydroxy-4H-1,3-benzoxazin-4-one, 41 g of 1,3-dibromo-propane and 10.4 g of potassium carbonate is stirred under reflux for 2½ hours. The reaction mixture is diluted with toluene and filtered and the filtrate is evaporated. 200 ml of ether are added to the residue and the sludge which has precipitated is filtered off. On evaporating the filtrate again and triturating the residue with 50 ml of petroleum ether, 14 g of crude 6-(3-bromo-propoxy)-2,3-dihydro-2,2-dimethyl-4H-1,3-benzoxazin-4-one are obtained in the form of a crystalline mass. After recrystallisation from a little petroleum ether, the product melts at 115°–118°.

EXAMPLE 23

A solution of 13.9 g of crude α-[N-benzyl-N-[3-(3-carbamoyl-4-hydroxy-phenyl)-propyl]-aminomethyl]-benzyl alcohol in 150 ml of methanol is hydrogenated under normal conditions in the presence of 1.4 g of palladium-on-charcoal catalyst (5%) until the absorption of hydrogen has ceased. On filtering the solution, evaporating the filtrate and triturating the residue with ether, a solid is obtained, which after recrystallisation from a little isopropanol is α-[N-[3-(3-carbamoyl-4-hydroxy-phenyl)-propyl]-aminomethyl]-benzyl alcohol with a melting point of 151°–153°.

The starting materials can be obtained in the manner described below:

(23a) 3-(4-Hydroxyphenyl)-propionic acid is converted via the mixed anhydride obtained with methyl chloroformate, using benzylamine, to 3-(4-hydroxyphenyl)-propionic acid N-benzylamide with a melting point of 115°–116°.

(23b) 3-(3-Carboxy-4-hydroxyphenyl)-propionic acid N-benzylamide with a melting point of 180°–181° is obtained from the sodium salt of 3-(4-hydroxyphenyl)-propionic acid N-benzylamide and carbon dioxide at a temperature of 180°, over a period of 4 hours and under a pressure of 55 bars, under the conditions of the Kolbe synthesis.

(23c) 3-(3-Methoxycarbonyl-4-hydroxyphenyl)-propionic acid N-benzylamide with a melting point of 139°–140° (from ethyl acetate) is obtained by esterifying 3-(3-carboxy-4-hydroxyphenyl)-propionic acid N-benzylamide with a mixture of methanol and concentrated sulfuric acid by refluxing for 48 hours.

(23d) 3-(4-Benzyloxy-3-methoxycarbonyl-phenyl)-propionic acid N-benzylamide is obtained in the form of a yellowish oil by reacting 3-(3-methoxycarbonyl-4-hydroxyphenyl)-propionic acid N-benzylamide with benzyl bromide in the presence of potassium carbonate in acetone as the solvent by refluxing for 15 hours.

(23e) Selective reduction of the amide group in 3-(4-benzyloxy-3-methoxycarbonyl-phenyl)-propionic acid N-benzylamide using diborane in tetrahydrofuran for a reaction time of 48 hours at a temperature of 20°–25° yields N-[3-(4-benzyloxy-3-methoxycarbonyl-phenyl)-propyl]benzylamine, which, in the form of the crude product, is converted by means of hydrogen in the presence of palladium-on-charcoal catalyst (50%), in methanol as the solvent, at a temperature of 15°–20° to N-[3-(4-hydroxy-3-methoxycarbonylphenyl)-propyl]-benzylamine with a melting point of 75°–77° (from isopropanol).

(23f) 200 ml of concentrated ammonia are added to a solution of 27 g of N-[3-(4-hydroxy-3-methoxycarbonylphenyl)-propyl]-benzylamine in 100 ml of dioxan und the mixture is left to stand for 3–4 days at 20°–30°. The reaction mixture is evaporated, the residue is partitioned between water and ethyl acetate and the organic phase is separated off. Customary working up yields 14.5 g of crude N-[3-carbamoyl-4-hydroxy-phenyl)-propyl]-benzylamine in the form of an oil; which is further processed without further purification.

(23g) A solution of 8.5 g of crude N-[3-(3-carbamoyl-4-hydroxyphenyl)propyl]-benzylamine and 10 g of phenylethylene oxide in 100 ml of isopropanol is refluxed for 8 hours and then evaporated. The oily residue is freed from excess phenylethylene oxide by stirring with petroleum ether. The crude, oily α-[N-benzyl-N-[3-(3-carbamoyl-4-hydroxyphenyl)-propyl]-aminomethyl]-benzyl alcohol, which is sparingly soluble in petroleum ether, is further processed in the form of the crude product, without further purification.

EXAMPLE 24

A solution of 31 g of crude N-[2-(3-carbamoyl-4-hydroxyphenoxy)-ethyl]-N-[2-(3,5-dibenzyloxy-phenyl)-2-hydroxy-ethyl]-benzylamine in 300 ml of methanol is hydrogenated under normal conditions over 6 g of palladium-on-charcoal catalyst (5%) until 3 mol equivalents of hydrogen have been taken up. The catalyst is filtered off, the filtrate is evaporated and the residue is dissolved in 200 ml of isopropanol. Filtering through silica gel and evaporating the filtrate yields α-[N-[2-(3-carbamoyl-4-hydroxyphenoxy)-ethyl-]aminomethyl]-3,5-dihydroxy-benzyl alcohol in the form of a brownish foam. After recrystallisation from ethylacetate/methanol the compound is obtained in pure state with a melting point of 203°–205°, and contains ¼ mol of crystal-water. The compound is characterised by the following signals in the proton nuclear magnetic resonance spectrum in hexadeuterodimethylsulfoxide as the solvent:

Chemical shift: 2.74 (d,2H); 3.0 (t,2H); 4.05 (t,2H); 4.5 (t,1H); 6.1 (d,1H); 6.24 (d,2H); 6.8 (d,1H); 7.05 (g,1H) and 7.47 (d,1H).

It has a melting point of 203°–205° (from ethyl acetate/methanol) having ¼ mol of crystal water.

The starting material can be prepared as follows:

(24a) 28.6 g of 5-(2-benzylamino-ethoxy)-salicylamide are added in portions, with stirring, to a solution of 20.6 g of ω-bromo-3,5-dibenzyloxy-acetophenone in 300 ml of acetone and the reaction mixture is stirred overnight at room temperature. The crystals which have precipitated are filtered off with suction and the filtrate is evaporated, yielding crude ω-[N-[2-(3-carbamoyl-4-hydroxy-phenoxy)ethoxy-ethyl]-benzylamino-3,5-dibenzyloxy-acetophenone.

(24b) Four 3 g portions of sodium borohydride are added at intervals of 2–3 hours to a solution of 39 g of the resulting crude product in a mixture of 200 ml of ethanol and 200 ml of methanol and the mixture is then stirred overnight. The pH of the mixture is adjusted to 4 by the dropwise addition of 2N hydrochloric acid, with ice-cooling, and the mixture is then evaporated. 200 ml of water are added to the evaporation residue and the mixture is rendered alkaline with concentrated ammonia solution and extracted with 400 ml of ethyl acetate. The organic phase is separated off, dried over magnesium sulfate and evaporated, yielding N-[2-(3-carbamoyl-4-hydroxyphenoxy)-ethyl]-N-[2-(3,5-dibenzyloxy-phenyl)-2-hydroxyethyl]benzylamine as a viscous crude product, which is further processed as such.

EXAMPLE 25

A suspension of 21.9 g of 5-(2-aminoethoxy)-salicylamide, 36.0 g of α-(bromomethyl)-benzyl alcohol and 30 g of potassium bicarbonate in 240 ml of ethanol is refluxed for 15 hours, with stirring. The reaction mixture is then cooled and filtered and the filtrate is evaporated. The evaporation residue is partitioned between 300 ml of ethyl acetate and 100 ml of water and the organic phase is separated off, dried over magnesium sulfate and evaporated. The residue is dissolved hot in as little ethanol as possible and made to crystallise, yielding α-[N-[2-(3-carbamoyl-4-hydroxy-phenoxy)ethyl]-aminomethyl]-benzyl alcohol with a melting point of 174°–175° (from ethanol).

EXAMPLE 26

A suspension of 14.5 g of phenylethylene oxide and 19.6 g of the 5-(2-aminoethoxy)-salicylamide, obtained according to Example (14a) in 50 ml of isopropanol is refluxed for 30 minutes. After cooling, α-[N-[2-(3-carbamoyl-4-hydroxy-phenoxy)-ethyl]-aminomethyl]-benzyl alcohol crystallises out gradually and after recrystallisation from ethanol melts at 174°–175°.

EXAMPLE 27

Tablets containing 20 mg of active ingredient are prepared in the following composition in the customary manner:

| Composition: | |
|---|---|
| α-N—[2-(3-Carbamoyl-4-hydroxy-phenoxy)-1-methyl-ethyl]-aminomethyl]-benzyl alcohol with a melting point of 152–154° | 20 mg |
| Corn starch | 60 mg |
| Lactose | 50 mg |
| Colloidal silica | 5 mg |
| Talc | 9 mg |
| Magnesium stearate | 1 mg |
| | 145 mg |

Preparation

α-[N-[2-(3-Carbamoyl-4-hydroxy-phenoxy)-1-methylethyl]-aminomethyl]-benzyl alcohol with a melting point of 152°–154° is mixed with a portion of the corn starch and with the lactose and colloidal silica and the mixture is forced through a sieve. A further portion of the corn starch is mixed to a paste with 5 times the amount of water on a waterbath and the pulverulent mixture is kneaded with this paste until a slightly plastic mass has formed.

The plastic mass is pressed through a sieve of about 3 mm mesh width and dried and the dry granules thus obtained are again forced through a sieve. The remainder of the corn starch, the talc and the magnesium-stearate are then mixed in and the mixture is compressed to tablets weighing 145 mg, which have a breaking notch.

EXAMPLE 28

Capsules containing 20 mg of active ingredient are prepared as follows in the customary manner:

| | |
|---|---|
| α-[N—[2-(3-Carbamoyl-4-hydroxy-phenoxy)-1-methyl-ethyl]-aminomethyl]-benzyl alcohol with a melting point of 152–154° | 2,500 mg |
| Talc | 80 mg |
| Colloidal silica | 20 mg |

Preparation

The active ingredient is intimately mixed with the talc and colloidal silica and the mixture is forced through a sieve of 0.5 mm mesh width and filled in 21 mg portions into hard gelatine capsules of suitable size.

EXAMPLE 29

A syrup containg 2% by weight/volume of active ingredient is prepared as follows in the customary manner:

| Composition: | |
|---|---|
| α-[N—[2-(3-Carbamoyl-4-hydroxy-phenoxy)-ethyl]-aminomethyl-benzyl alcohol with a melting point of 152–154° | 2.0 g |
| Saccharin | 0.6 g |
| Sugar | 30.0 g |
| Glycerin | 5.0 g |
| Flavourings | 0.1 g |
| Ethanol (86%) | 10.1 ml |
| Distilled H$_2$O | to make up to 100 ml |

Preparation

The sugar, saccharin and glycerin are dissolved in 60 g of water. The solution of the active ingredient and of the flavouring in ethanol is added to this solution, with stirring. The mixture is then made up to 100 ml with distilled water.

EXAMPLE 30

In place of the compounds used as the active ingredient in Examples 27 to 29, it is also possible to use the following compounds of the formula I, or their pharmaceutically acceptable non-toxic acid addition salts, as active ingredients in tablets, sugar-coated tablets, capsules and the like: α-[N-[2-(4-carbamoyl-3-hydroxyphenoxy)-1-methyl-ethyl]-aminomethyl]-benzyl alcohol in the form of the enantiomer pair with a melting point of 171°–173° or in the form of the enantiomer pair with a melting point of 149°–151°; α-[N-[2-(4-carbamoyl-3-hydroxy-phenoxy)-ethyl]-aminomethyl]-benzyl alcohol, α-[N-[2-(3-carbamoyl-4-hydroxy-phenoxy)-1-methyl-ethyl]-aminomethyl]-3-pyridinemethanol, α-[N-[2-(3-carbamoyl-4-hydroxy-phenoxy)-1-methyl-ethyl]-aminomethyl]-4-hydroxybenzyl alcohol, R-(—)-α-[N-[2-(3-carbamoyl-4-hydroxy-phenoxy)-1-methyl-ethyl]-aminomethyl]-benzyl alcohol, α-[N-[2-(3-carbamoyl-4-hydroxy-phenoxy)-ethyl]-aminomethyl]-4-hydroxybenzyl alcohol, α-[N-[2-(2-carbamoyl-3-hydroxyphenoxy)-ethyl]-aminomethyl]-benzyl alcohol, α-[N-[3-(4-carbamoyl-3-hydroxy-phenoxy)-propyl]-aminomethyl]-benzyl alcohol, α-[N-[2-(3-carbamoyl-4-hydroxy-phenoxy)-ethyl]-aminomethyl]-benzyl alcohol, α-[N-[2-(3-carbamoyl-4-hydroxyphenoxy)-ethyl]-aminomethyl-2-pyridinemethanol, α-[N-[3-(3-carbamoyl-4-hydroxy-phenoxy)-propyl-aminomethyl]-benzyl alcohol, α-[N-[2-(3-carbamoyl-4-hydroxy-phenoxy)-ethyl]-aminomethyl]-2-furanmethanol, α-[N-[2-(3-carbamoyl-4-hydroxy-phenoxy)-ethyl]-aminomethyl]-2-thiophenmethanol, the enantiomer of S(+)-α-[N-[2-(3-carbamoyl-4-hydroxyphenoxy)-1-methyl-ethyl]-aminomethyl]-benzyl alcohol which has a melting point of 160°–162° (melting point of the hydrochloride 189°–191°) or the enantiomer for which the hydrochloride has a melting point of 181°–183°, α-[N-[2-(4-carbamoyl-3-hydroxyphenoxy)-ethyl]-aminomethyl]-4-hydroxybenzyl alcohol, α-[N-[3-(3-carbamoyl-4-hydroxyphenoxy)-propyl]-aminomethyl]-benzyl alcohol, α-[N-[3-(3-carbamoyl-4-hydroxy-phenoxy)-propyl]-aminomethyl]-benzyl alcohol, α-[N-[2-(3-carbamoyl-4-hydroxy-phenoxy]-ethyl]-aminomethyl]-3,5-dihydroxybenzyl alcohol, α-[N-[2-(3-carbamoyl-4-hydroxy-phenoxy)-1,1-dimethyl-ethyl]-aminomethyl]-benzyl alcohol, R-(—)-α-[N-[2-(3-carbamoyl-4-hydroxyphenoxy)-1,1-dimethyl-ethyl]-aminomethyl]-benzyl alcohol, (R)-(—)-α-[N-[2-(3-carbamoyl-4-hydroxy-phenoxy)-ethyl]-aminomethyl]-benzyl alcohol, S-(+)-α-[N-[2-(3-carbamoyl-4-hydroxyphenoxy)-ethyl]-aminomethyl]-benzyl alcohol or α-[N-[4-(3-carbamoyl-4-hydroxy-phenoxy)-butyl]-aminomethyl]-benzyl alcohol.

EXAMPLE 31

A solution of 4.5 g of 5-(2-amino-2-methyl-propoxy)-salicylamide and 3.1 g of 2-phenyloxirane in 40 ml of dioxane is refluxed for 16 hours. The solvent is subsequently evaporated off under reduced pressure, and the residue is dissolved in 20 ml of 2N hydrochloric acid, and extracted with 50 ml of ether. The water phase is separated; it is rendered alkaline with concentrated ammonia, and the liberated base is extracted with 200 ml of ethyl acetate. Customary further processing yields a light-coloured foam, from which is obtained, by recrystallisation from isopropanol, α-[N-[2-(3-carbamoyl- 4-hydroxy-phenoxy)-1,1-dimethyl-ethyl]-aminomethyl]-benzyl alcohol, m.p. 121°-123°. It forms a neutral fumarate, m.p. 209°-210° (from methanol).

There is obtained in an analogous manner, with the use of (R)-2-phenyloxirane, (R)-(−)-α-[N-[2-(3-carbamoyl-4-hydroxyphenoxy)-1,1-dimethyl-ethyl]-aminomethyl]-benzyl alcohol in the form of a yellowish oil.

5-(2-Amino-2-methyl-propoxy)-salicylamide required as starting material is produced in the following manner:

(a) By the method described by Irvine et al., Synthesis 1972, 568, 2,5-dihydroxy-benzamide is converted, using an excess of acetone, into 2,3-dihydro-2,2-dimethyl-6-hydroxy-4H-1,3-benzoxazin-4-one, m.p. 215°-216° C.

(b) A mixture of 84.3 g of 2,3-dihydro-2,2-dimethyl-6-hydroxy-4H-1,3-benzoxazin-4-one, 144.2 g of methanesulfonic acid-(2-methyl-2-nitropropyl)-ester and 121 g of anhydrous potassium carbonate in 440 ml of diethylene glycol dimethyl ether is stirred for 9 hours in a bath at about 150°. The reaction mixture is cooled, poured into 4000 ml of water, and extracted with 3000 ml of ethyl acetate. The oil, obtained by concentrating the organic phase by evaporation, is dissolved in 250 ml of dioxane, and about 750 ml of 2N hydrochloric acid is added until an acid reaction occurs. The solution is held for 1½ hours at 80°-100°; it is then concentrated under reduced pressure to half its volume, and extracted three times with 500 ml of ethyl acetate each time. The combined organic phases are washed with 200 ml of water, then with saturated sodium bicarbonate solution, and finally with saturated sodium chloride solution; they are subsequently dried over magnesium sulfate and concentrated by evaporation. The dark brown oil thus obtained is chromatographed on 500 g of silica gel. Elution with ether yields crystalline 5-(2-methyl-2-nitropropoxy)-salicylamide, m.p. 145°-148°.

(c) 11.5 g of 5-(2-methyl-2-nitro-propoxy)-salicylamide in 150 ml of methanol is hydrogenated at 40°-50° and 80 bars, with 5 g Raney Nickel, until the absorption of hydrogen ceases. Filtration and concentration by evaporation of the reaction mixture yield crude 5-(2-amino-2-methyl-propoxy)-salicylamide, which on prolonged standing crystallises from isopropanol, and melts at 115°-117°.

EXAMPLE 32

A solution of 23 g of crude (R)-α-[N-benzyl-N-[2-(3-carbamoyl-4-hydroxy-phenoxy)-ethyl]-aminomethyl]-benzyl alcohol in 230 ml of methanol is hydrogenated, with the addition of 5 g of palladium-charcoal catalyst (5%), under normal conditions until 1 mol-equivalent of hydrogen has been absorbed. The catalyst is subsequently filtered off, is washed with methanol, and the combined methanolic solutions are concentrated under reduced pressure. The crystalline residue is recrystallised from methanol and yields (R)-(−)-α-[N-[2-(3-carbamoyl-4-hydroxy-phenoxy)-ethyl]-aminomethyl]-benzyl alcohol, m.p. 166°-172°; $[\alpha]_D = -23° \pm 1°$ (C=0.6% in methanol).

With the use of (S)-α-[N-benzyl-N-[2-(3-carbamoyl-4-hydroxy-phenoxy)-ethyl]-aminomethyl]-benzyl alcohol as starting material, there is obtained (S)-(+)-α-[N-[2-(3-carbamoyl-4-hydroxy-phenoxy)-ethyl]-aminomethyl]-benzyl alcohol, m.p. 166°-172°; $[\alpha]_D = +23° \pm 1°$ (c=0.6% in methanol).

Starting material is produced in the following manner:

(a) A suspension of 60 g of 6-(2-bromoethoxy)-2,3-dihydro-2,2-dimethyl-4H-1,3-benzoxazin-4-one in 110 ml of benzylamine is heated, with stirring, for 30 minutes in a bath at 80°. The reaction mixture is thereupon adjusted with conc. hydrochloric acid, using ice-cooling, to a pH value of about 3, and is allowed to stand until crystallisation occurs. The crystals are filtered off with suction after 4 hours, washed with 100 ml each of water and of ethyl acetate, and dried. The crude 5-(2-benzylamino-ethoxy)-salicylamide hydrochloride obtained melts at 214°-216°. The base liberated therefrom melts at 107°-108° (from ethyl acetate/ether).

(b) A solution of 7.2 g of (R)-2-phenyl-oxirane and 14.3 g of 5-(2-benzylamino-ethoxy)-salicylamide in 100 ml of isopropanol is refluxed for 22-24 hours. The solution is concentrated by evaporation to yield (R)-α-[N-benzyl-N-[2-(3-carbamoyl-4-hydroxy-phenoxy)-ethyl]-aminomethyl]-benzyl alcohol, which is further processed in this form.

EXAMPLE 33

A mixture of 5.8 g of α-(aminomethyl)-benzyl alcohol and 6.6 g of 2,3-dihydro-2,2-dimethyl-6-(4-bromobutoxy)-4H-1,3-benzoxazin-4-one is melted in an oil bath at 120°-130°, and the melt is stirred for 1 hour at this temperature. After cooling to 50°-60°, the reaction mixture is dissolved in the smallest possible amount of isopropanol; the solution is then filtered with the addition of kieselguhr and cooled. In this manner crystallises α-[N-[4-(3-carbamoyl-4-hydroxy-phenoxy)-butyl]-aminomethyl]-benzyl alcohol as hydrobromide, m.p. 154°-155°.

The starting material is produced in the following manner.

(a) A suspension of 96.5 g of 2,3-dihydro-2,2-dimethyl-6-hydroxy-4H-1,3-benzoxazin-4-one and 76 g of potassium carbonate in 300 ml of 1,4-dibromobutane is stirred for 5 hours in a bath at 120°-130°. The reaction mixture is filtered, and the excess 1,4-dibromobutane is distilled off at about 1 Torr. The crystalline residue is triturated with ether, and filtered off under suction. There is thus obtained crude 2,3-dihydro-2,2-dimethyl-6-(4-bromobutoxy)-4H-1,3-benzoxazin-4-one, m.p. 139°-142°, which is sufficiently pure for the further reaction.

EXAMPLE 34

1.6 g of (R)-2-phenyloxirane is added to a solution of 2.0 g of 5-(2-aminoethoxy)-salicylamide in 30 ml of dioxane, and the whole is refluxed for 3 hours. The solvent is evaporated off; the residue is triturated with 30 ml of ether, and the ether-insoluble part is dissolved in the smallest possible amount of methanol. There gradually crystallises (R)-(−)-α-[N-[2-(3-carbamoyl-4-hydroxyphenoxy)-ethyl]-aminomethyl]-benzyl alcohol, which melts at 166°-172° after recrystallisation from methanol.

With the use of (S)-2-phenyloxirane as starting material, there is correspondingly obtained (S)-(+)-α-[N-[2-(3-carbamoyl-4-hydroxyphenoxy)-ethyl]-aminomethyl]-benzyl alcohol, m.p. 166°-172°; $[\alpha]_D = +23 \pm 1°$ (c=0.6% in methanol).

The 5-(2-aminoethoxy)-salicylamide required as starting material is obtained as follows:

(a) The 5-(2-aminoethoxy)-salicylamide required as starting material is obtained by catalytic debenzylation of 5-(2-benzylamino-ethoxy)-salicylamide by means of a 5% palladium-charcoal catalyst in methanol under normal conditions. After the hydrogen absorption is completed, the catalyst is filtered off, and the filtrate is concentrated under reduced pressure to thus obtain 5-(2-aminoethoxy)-salicylamide, m.p. 140°.

EXAMPLE 35

0.8 g of sodium borohydride is added portionwise, with ice-cooling, to a solution of 2.7 g of crude α-[N-[2-(3-carbamoyl-4-hydroxy-phenoxy)-ethylidene]-iminomethyl]-benzyl alcohol in 40 ml of ethanol, and the reaction mixture is stirred at 20°-30° for 3 hours. With application of ice-cooling, the reaction mixture is decomposed with 2N hydrochloric acid, and then concentrated under reduced pressure. The residue is rendered alkaline with ammonia solution (10%), and is extracted three times with 100 ml of ethyl acetate each time. After drying of the organic phase over sodium sulfate and concentration by evaporation, there is obtained an oil which, after recrystallisation from methanol, yields α-[N-[2-(3-carbamoyl-4-hydroxy-phenoxy)-ethyl]-aminomethyl]-benzyl alcohol, m.p. 174°-175°.

The starting material is produced in the following manner:

(a) A solution of 9.65 g of 2,3-dihydro-2,2-dimethyl-6-hydroxy-4H-1,3-benzoxazin-4-one and 9.1 g of allyl bromide in 150 ml of acetonitrile, with the addition of 10.3 g of anhydrous potassium carbonate, is refluxed for 5 hours. The reaction mixture is filtered warm; the filtrate is then concentrated by evaporation and, after trituration with ether, the crystals remaining are filtered off with suction. The crude 2,3-dihydro-2,2-dimethyl-6-(1-propen-3-yloxy)-4H-1,3-benzoxazin-4-one thus obtained melts at 137°-138°

(b) About 20 mg of osmium tetroxide is added, with stirring, to a solution of 4.7 g of 2,3-dihydro-2,2-dimethyl-6-(1-propen-3-yloxy)-4H-1,3-benzoxazin-4-one in a mixture of 50 ml of dioxane and 15 ml of water. After 15 minutes, there is added in portions 8.6 g of sodium metaperiodate, in the course of which the temperature rises to 45°. The reaction mixture is filtered after 2 hours; the filtrate is concentrated by evaporation, and the residue is distributed between 20 ml of water and 200 ml of ethyl acetate. The organic phase is separated, dried over sodium sulfate and concentrated by evaporation, and the oil obtained is chromatographed on 100 g of silica gel. By elution with ethyl acetate and concentration by evaporation, there is obtained (2,3-dihydro-2,2-dimethyl-4H-1,3-benzoxazin-4l-on-6-yloxy)-acetaldehyde, m.p. 153°-163°.

(c) A solution of 1.64 g of α-(aminomethyl)-benzyl alcohol and 2.23 g of (2,3-dihydro-2,2-dimethyl-4H-1,3-benzoxazin-4-on-6-yloxy)-acetaldehyde in 20 ml of anhydrous ethanol is refluxed for 3 hours. The solution obtained is concentrated by evaporation to yield crude α-[N-[2-(3-carbamoyl-4-hydroxy-phenoxy)-ethylidene]-iminomethyl]-benzyl alcohol, which is further processed in this form.

What is claimed is:

1. A compound of the formula

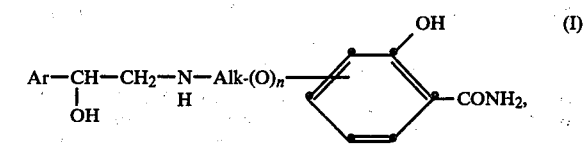

in which Ar is phenyl or pyridyl unsubstituted or substituted by 1 or 2 hydroxyl groups, n has the values 0 or 1 and Alk is an alkylene radical having 2 to 5 carbon atoms, and the nitrogen atom and the oxygen atom appearing in the group

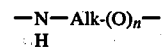

or, if n is 0, the salicylamide radical, are separated from one another by at least 2 carbon atoms, in the form of racemates, a mixture of racemates, or an optical antipode, or a pharmaceutically acceptable non-toxic acid addition salt thereof.

2. A compound as claimed in claim 1, which is alpha-[N-[2-(3-Carbamoyl-4-hydroxy-phenoxy)-1-methylethyl]-aminomethyl]-benzyl alcohol.

3. The enantiomer pair of the compound of claim 2 with a melting point of 166°-168°.

4. The enantiomer pair of the compound of claim 2 with a melting point of 152°-154°.

5. A compound as claimed in claim 1, which is alpha-[N-[2-(3-Carbamoyl-4-hydroxy-phenoxy)-1-methylethyl]-amino methyl]-3-pyridinemethanol.

6. A compound as claimed in claim 1, which is alpha-[N-[2-(3-Carbamoyl-4-hydroxy-phenoxy)-1-methylethyl]-aminoethyl-2-pyridinemethanol.

7. A compound as claimed in claim 1, which is alpha-[N-[2-(3-carbamoyl-4-hydroxy-phenoxy)-1,1-dimethylethyl]-aminomethyl]-benzyl alcohol.

8. A compound as claimed in claim 1, which is alpha-[N-[4-(3-carbamoyl-4-hydroxy-phenoxy)-butyl]-aminomethyl]-benzyl alcohol.

9. A compound as claimed in claim 1, which is alpha-[N-[2-(4-Carbamoyl-3-hydroxy-phenoxy)-1-methylethyl]-aminomethyl]-benzyl alcohol.

10. The enantiomer pair of the compound of claim 9 with a melting point of 171°-173°.

11. The enantiomer pair of the compound of claim 9 with a melting point of 149°-151°.

12. A compound as claimed in claim 1 which is alpha-[N-[2-(3-Carbamoyl-4-hydroxy-phenoxy)-ethyl]-aminomethyl]-benzyl alcohol.

13. A compound as claimed in claim 1 which is alpha-[N-[2-(4-Carbamoyl-3-hydroxy-phenoxy)-ethyl]-aminomethyl]-benzyl alcohol.

14. The hydrochloride salt of the compound of claim 13.

15. The neutral fumarate salt of the compound of claim 5.

16. A compound as claimed in claim 1 which is alpha-[N-[2-(3-Carbamoyl-4-hydroxy-phenoxy)-1-methylethyl]-aminomethyl]-2-pyridinemethanol.

17. The neutral fumarate salt of the compound of claim 16.

18. A compound as claimed in claim 1 which is alpha-[N-[2-(3-Carbamoyl-4-hydroxy-phenoxy)-1-methylethyl]-aminomethyl]-4-hydroxybenzyl alcohol.

19. The fumarate salt of the compound of claim 18.

20. The enantiomer pair of the compound of claim 19 with a melting point of 209°–212° (decomposition).

21. A compound as claimed in claim 1 which is R-(−)-alpha-[N-[2-(3-Carbamoyl-4-hydroxy-phenoxy)-1-methylethyl]-aminomethyl]-benzyl alcohol.

22. The hydrochloride salt of the compound of claim 21.

23. The enantiomer of the compound of claim 22 with a melting point of 180°–184°.

24. A compound as claimed in claim 1 which is alpha-[N-[2-(3-Carbamoyl-4-hydroxy-phenoxy)-ethyl]-aminomethyl]-4-hydroxybenzyl alcohol.

25. A compound as claimed in claim 1 which is alpha-[N-[2-(2-Carbamoyl-3-hydroxy-phenoxy)-ethyl]-aminomethyl]benzyl alcohol.

26. The hydrochloride salt of the compound of claim 25.

27. A compound as claimed in claim 1 which is alpha-[N-[3-(4-Carbamoyl-3-hydroxy-phenoxy)-propyl]-aminomethyl]-benzyl alcohol.

28. A compound as claimed in claim 1 which is alpha-[N-[2-(3-Carbamoyl-4-hydroxy-phenoxy-ethyl]-aminomethyl]-2-pyridinemethanol.

29. A compound as claimed in claim 1 which is S-(+)-[N-[2-(3-Carbamoyl-4-hydroxy-phenoxy-1-methylethyl]-aminomethyl]-benzyl alcohol.

30. The enantiomer of the compound of claim 29 with a melting point of 160°–162°.

31. The enantiomer of the compound of claim 30 in the form of the hydrochloride salt.

32. A compound as claimed in claim 1 which is alpha-[N-[2-(4-Carbamoyl-3-hydroxy-phenoxy)-ethyl]-aminomethyl]-4-hydroxy-benzyl alcohol.

33. A compound as claimed in claim 1 which is alpha-[N-[3-(3-Carbamoyl-4-hydroxy-phenoxy)-propyl]-aminomethyl]-benzyl alcohol.

34. The hydrochloride salt of the compound of claim 33.

35. A compound as claimed in claim 1 which is alpha-[N-[3-(3-Carbamoyl-4-hydroxy-phenyl)-propyl]-aminomethyl]-benzyl alcohol.

36. A compound as claimed in claim 1 which is alpha-[N-[2-(3-Carbamoyl-4-hydroxy-phenoxy)-ethyl]-aminomethyl]-3,5-dihydroxybenzyl alcohol.

37. A compound as claimed in claim 1 which is (R)-(−)-alpha-[N-[2-(3-carbamoyl-4-hydroxy-phenoxy)-1,1-dimethyl-ethyl]-aminoethyl]-benzyl alcohol.

38. A compound as claimed in claim 1 which is (R)-(−)-alpha-[N-[2-(3-carbamoyl-4-hydroxy-phenoxy)-ethyl]-aminoethyl]-benzyl alcohol.

39. A compound as claimed in claim 1 which is (S)-(+)-alpha-[N-[2-(3-carbamoyl-4-hydroxy-phenoxy)-ethyl]-aminomethyl]-benzyl alcohol.

40. A pharmaceutical composition useful as a cardioselective β-stimulator for the treatment of cardiac insufficiency comprising a therapeutically effective amount of a compound of the formula I as claimed in claim 1 or a pharmaceutically acceptable non-toxic acid addition salt thereof together with a pharmaceutically usable carrier.

41. A method for the treatment of cardiac insufficiency in a warm-blooded animal which comprises administering a therapeutically effective amount of a compound of the formula I defined in claim 1 to an animal in need thereof.

* * * * *